United States Patent [19]

Potter et al.

[11] Patent Number: 5,521,072
[45] Date of Patent: May 28, 1996

[54] ACTINOBACILLUS PLEUROPNEUMONIAE TRANSFERRIN BINDING PROTEINS AND USES THEREOF

[75] Inventors: Andrew A. Potter; Gerald F. Gerlach; Philip J. Willson; Amalia Rossi-Campos, all of Saskatoon, Canada

[73] Assignee: University of Saskatchewan, Saskatoon, Canada

[21] Appl. No.: 217,438

[22] Filed: Mar. 22, 1994

Related U.S. Application Data

[63] Continuation of Ser. No. 961,522, Oct. 15, 1992, Pat. No. 5,417,971, which is a continuation-in-part of Ser. No. 780,912, Oct. 22, 1991, abandoned.

[51] Int. Cl.$^6$ .............................. C12N 15/31; C12N 1/21; C12P 21/00
[52] U.S. Cl. .................. 435/69.3; 435/252.3; 435/240.1; 435/254.11; 435/320.1; 536/23.7
[58] Field of Search ........................ 536/23.7; 435/69.1, 435/69.3, 252.3, 252.33, 320.1, 172.3, 240.1, 254.11; 935/12, 65

[56] References Cited

U.S. PATENT DOCUMENTS 5,141,743   8/1992   Schryvers .............................. 530/350

FOREIGN PATENT DOCUMENTS

| 420743 | 4/1991 | European Pat. Off. . |
| 453024 | 10/1991 | European Pat. Off. . |
| WO90/12591 | 11/1990 | WIPO . |
| WO91/04747 | 4/1991 | WIPO . |
| WO91/06653 | 5/1991 | WIPO . |

OTHER PUBLICATIONS

Boswell, P. R. et al. 1988. In: *Computational Molecular Biology*, ed. A. M. Lesk, Oxford Univ. Press, pp. 161–178..
Gonzalez, G. C. et al. 1990. *Molecular Microbiology* vol. 4 pp. 1173–1179.
Smeltzer, M. S. 1990. *Dissertation Abstracts Intl.* vol. 51/06–B, p. 2740.
Corbeil, L. B. et al. 1988. *Infection & Immunity* vol. 56 pp. 2736–2742.
Anderson et al., *Infect. Immun.* (1991) 59:4110–4116.
Archibald, F. S., and DeVoe, I. W., *FEMS Microbiol. Lett.* (1979) 6:159–162.
Archibald, F. S., and DeVoe, I. W., *Infect. Immun.* (1980) 27:322–334.
Chang et al., *DNA* (1989) 8:635–647.
Deneer, H. G., and Potter, A. A., *Infect. Immun.* (1989) 57:798–804.
Frey et al., *Infect. Immun.* (1991) 59:3026–3032.
Gerlach, G. F., et al., *Infect. Immun.* (1992) 60:892–898.
Gerlach, G. F., et al. (1992) *Infect. Immun.* 60:3253–3261.
Gonzalez et al., *Mol. Microbiol.* (1990) 4:1173–1179.
Herrington, D. A., and Sparling, F. P., *Infect. Immun.* (1985) 48:248–251.
Higgins et al., *Can. Vet. J.* (1985) 26:86–89.
Kamp et al., Abstr. *CRWAD* (1990) 1990:270.
MacInnes, J. I., and Rosendal, S., *Infect. Immun.* (1987) 55:1626–1634.
Rycroft et al., *J. Gen. Microbiol.* (1991) 137:561–568.
Rossi–Campos, A., et al., *Vaccine* (1992) 10:512–518.
Weinberg, E. D., *Microbiol. Rev.* (1978) 42:45–66.
Welch, R. A., *Mol. Microbiol.* (1991) 5:521–528.

*Primary Examiner*—Mary E. Mosher
*Attorney, Agent, or Firm*—Reed & Robins

[57] ABSTRACT

Novel vaccines for use against *Actinobacillus pleuropneumoniae* are disclosed. The vaccines contain at least one *A. pleuropneumoniae* transferrin binding protein and/or one *A. pleuropneumoniae* cytolysin and/or one *A. pleuropneumoniae* APP4. Also disclosed are DNA sequences encoding these proteins, vectors including these sequences and host cells transformed with these vectors. The vaccines can be used to treat or prevent porcine respiratory infections.

16 Claims, 20 Drawing Sheets

```
          10         20         30         40         50         60         70         80         90        100        110        120
           *          *          *          *          *          *          *          *          *          *          *          *
ACAATGCCAATTAACCAATCTATTCCACTTGAATTACCAACCTCCAGTATTGAGAAAAAGATGAGCCAAAATATCTTCAGAGTGGCGATAATCCTACGGGCATTATTTAGGC
TGTTACGGTTATAATTGGGTTAGATAAGGTTGAACTTAATGTTGGAGGTCATAACTCTTTTTTCTACTCGGTTCTTCTATAGAAGTCCCGTAATAAGGATGCCCGTAAATAATCCG 130        140        150        160        170        180        190        200        210        220        230        240
           *          *          *          *          *          *          *          *          *          *          *          *
GAGAAGCTAGTGAATGAAGAGAATAAAACAATCTTTTCTGACAAAATTCAGGAAAATAAAAATACCGTTATTGCTATTTCTGCGGATAATTCCGTGGAATATCAACATATCGTGAAA
CTCTTCGATCACTTACTTCTCTTTTATTTGTTTAGAAATGACTGTTTTAAAGTCCTTTATTTTATGGCAATAACGATAAAGACGCCTATAAAGGTGTATAGCACTTT 250        260        270        280        290        300        310        320        330        340        350
           *          *          *          *          *          *          *          *          *          *          *
GTCCTTGAATTAGCTCAAAACGTCGGGCTAACGAAATAGGCTTTGTGACTCACCTAGTAATAAAGCAGAAATTTATATTGGAGGCAAT ATG CAT TTT AAA CTT AAT CCC
CAGGAACTTAATCGAGTTTGCAGCCCGATTGCTTTTATCCGAAACACTGAGTGATCATTATTTCGTCTTTAAATATAACCCTCCGTTA TAC GTA AAA TTT GAA TTA GGG
                                                                                          Met His Phe Lys Leu Asn Pro>
                                                                                          OPEN READING FRAME_a_____

360        370        380        390        400        410        420        430        440
           *          *          *          *          *          *          *          *          *
TAT GCG TTA GCG TTT ACT TCG CTG TTT CTT GTC GCT TGT TCT GGC AAA GGA AGT TTT GAT TTA GAA GAT GTC CGG CCT AAT AAG ACA
ATA CGC AAT CGC AAA TGA AGC GAC AAA GAA CAG CGA ACA AGA CCG TTT CCT TCA AAA CTA AAT CTT CTA CAG GCC GGA TTA TTC TGT
Tyr Ala Leu Ala Phe Thr Ser Leu Phe Val Ala Cys Ser Gly Lys Gly Ser Phe Asp Leu Glu Asp Val Arg Pro Asn Lys Thr>
_____a_____a_____a_____a__ OPEN READING FRAME____a_____a_____a_____a_____ )

450        460        470        480        490        500        510        520        530
           *          *          *          *          *          *          *          *          *
ACA GGC GTG TCT AAA GAG GAG TAC ATG AAG GAT CTA CAT ATG GTA CAT GAA ACA GCC AAG AAA GAA TTT CTT GGG TTA ATG GAA CCT GCT TTG GGG
TGT CCG CAC AGA TTT CTC CTC ATG TAC TTC CTA GAT GTA TAC CAT GTA CTT TGT CGG TTC TTT CTT CCC AAT GTC CTT GGA CGA AAC CCC
Thr Gly Val Ser Lys Glu Glu Tyr Met Lys Asp Leu His Met Val His Glu Thr Ala Lys Lys Glu Phe Leu Gly Leu Met Glu Pro Ala Leu Gly>
_____a_____a_____a_____a_____a__ OPEN READING FRAME____a_____a_____a_____ )

540        550        560        570        580        590        600        610        620
           *          *          *          *          *          *          *          *          *
TAT GTT GTA AAA GTT CCG GTG AGT TCT TTT GAA AAT TTA AAG GTT GAT ATT TCA GAT ATA GAA GTG ATT ACG AAC GGA AAT TTA GAC GAT
ATA CAA CAT TTT CAA GGC CAC TCA AGA AAA CTT TTA AAT TTC CAA CTT TAA AGT CTA TAT CTT CAC TAA TGC TTG CCT TTA AAT CTG CTA
Tyr Val Val Lys Val Pro Val Ser Ser Phe Glu Asn Leu Lys Val Asp Ile Ser Asp Ile Glu Val Ile Thr Asn Gly Asn Leu Asp Asp>
_____a_____a_____a_____a_____a__ OPEN READING FRAME____a_____a_____a_____ )
```

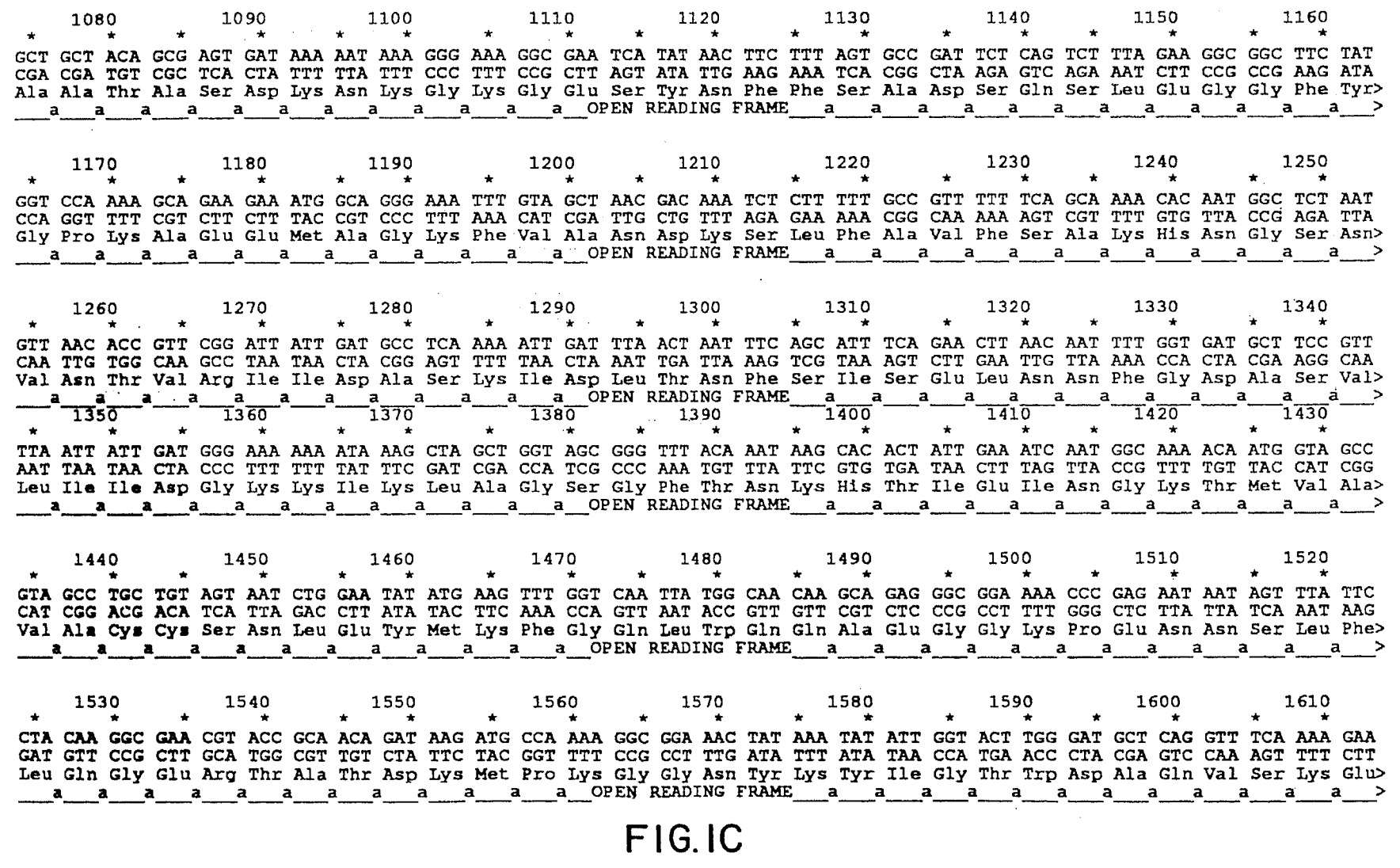

```
        1620        1630        1640        1650        1660        1670        1680        1690        1700
         *           *           *           *           *           *           *           *           *
AAT AAC TGG GTT GCT ACG GCA GAT GAT CTA CTA GAT AGA AAA GCT CGA TCT CGG ACA TAT GGC TAT TTT GAT GTT CAA GAA AAA AAT TTA AGT GGT
TTA TTG ACC CAA CGA TGC CGT GCA CTA GAT TTT CGA GCT AGC TGT CTT AAA CTA GCC CGT ATA CCG TGT CTT AAA CCG TTG TTT TTA TCA CCA
Asn Asn Trp Val Ala Thr Ala Asp Asp Leu Leu Asp Arg Lys Ala Arg Ser Arg Thr Tyr Gly Tyr Phe Asp Val Gln Glu Lys Asn Leu Ser Gly>
 a           a           a          a  OPEN READING FRAME  a           a          a          a          a           ^

1710        1720        1730        1740        1750        1760        1770        1780        1790
         *           *           *           *           *           *           *           *           *
AAG TTA TTT GAT AAA AAC GGT GTA CAT TTA GGA CAC AAA TGG TTT ACC GTG TTT AAT CCT GTA GAT GGT GCA AAA ATT TAA CTA CGT CTA CCA AAA ATT GGT TTT ACT GGC AAA GCT AAA ACC TCA
TTC AAT AAA CTA TTT TTG CCA CGA GAT AGT CTA GTG TTT ACC AAA TGG CAC AAA TTA GGA CAT CTA CCA TTT AAA TTA CCA CAA TTA CCA CGT TTT CGA TGG TTT CGA
Lys Leu Phe Asp Lys Asn Gly Val His Leu Gly His Lys Trp Phe Thr Val Phe Asn Pro Val Asp Gly Ala Lys Ile Asp Gly Phe Thr Gly Lys Ala Lys Thr Ser>
 a           a           a           a           a           a  OPEN READING FRAME  a           a           a           ^

1800        1810        1820        1830        1840        1850        1860        1870        1880
         *           *           *           *           *           *           *           *           *
GAT GAA GGC TTC CTA GAT CTA AGT TCA CGT AGT TCA TAT GAG AAT GTG AAA TTT AAA GAT GTA GCA GTT CAA GTA AGT GGT GGC TTC TAT GGT CCA
CTA CTT CCG AAG CGA GAT GAT CTC AGT TCA TCA AGT ATA CTC TTA CAC TTT AAA TTG CTA CAT CGT CAA TCA CCA CCG AAG ATA CCA GGT
Asp Glu Gly Phe Leu Asp Leu Ser Ser Arg Ser Ser Tyr Glu Asn Val Lys Phe Lys Asp Val Ala Val Gln Val Ser Gly Gly Phe Tyr Gly Pro>
 a           a           a           a           a           a           a           a  OPEN READING FRAME   ^

1890        1900        1910        1920        1930        1940        1950        1960        1970
         *           *           *           *           *           *           *           *           *
ACG GCA GCA GAG CTT GAA CCG GGA CCT GTT AAG GTG GTA TCA GAA AAT GGC AGT GTC TTT GGT GCT GTC GCA AAA CAA GTA CAA AAA
TGC CGT CGT CTC GAA CTT GGC CCT GGA CAA CCG TTC CAC CAT AAA TCA GAA CTT TTA CCG GTA TTT AGT CTT TCG ATA CGT CCA CAG CGT TTT CAT TTT GTT
Thr Ala Ala Glu Leu Glu Pro Gly Pro Val Lys Val Val Ser Glu Asn Gly Ser Val Phe Gly Ala Val Phe Gly Ala Lys Gln Val Lys Lys>
 a           a           a           a  OPEN READING FRAME   a           a           a           a 1980        1990        2000        2010        2020        2030        2040        2050        2060        2070        2080        2090
         *           *           *           *           *           *           *           *           *           *           *           *
TAA TAAGGAATTTGCAATGCAATAAAAATAAATTAAATCGATTAGCTTGCTCTGCTTAGCCTCTCTTGCCTACAAAGCTATGCAGAACAAGCGGTGCAATGAACGATGTTTATGTCACAGG
ATT ATTCCTTAAACGTTACTTTTTATTTAATTTAGACTAATCGAACGAGACGAATCGGAGAACGCATGTTTCGATACGTCTTGTTCGCCACGTTAACTTGCTACAAATACAGTCC
End>
 ^

2100        2110        2120        2130        2140        2150        2160        2170        2180        2190        2200        2210
         *           *           *           *           *           *           *           *           *           *           *           *
TACCAAAAAGAAAGCACATAAAAAGAGAACGAAGTGACAGGCTTAGGGAAAGTAGTGAAAACACCAGATTCTCTTAGTAAGGAGCAAGTGTTAGGAGAATGCGAGATCCTGAGATCCTGCTACGA
ATGGTTTTTCTTTCGTGTATTTTCGTCCTGCTCACTGTCCGAATCCTTAGGTCCTAAGAATCATTCCTCGTTCACAATCCTTACGCTCTAGACTGAGACTGT
```

FIG.1D

```
        2220      2230      2240      2250      2260      2270      2280      2290      2300      2310      2320      2330
          *         *         *         *         *         *         *         *         *         *         *         *
TCCGGGTATTCTGTAGTAGAGCAAGGACGAGGTGCAACGACAGGCTACTCAATTCGTGGGTAGATCGTAATCGTGTGGCTTGGCATTAGACGGTTTGCCACAGATTCAATCCTATGT
AGGCCCATAAGACATCATCTCGTTCCTGCTCCACGTTGCGTCCGATGAGTTAAGCACCCATCTAGCATTAGCACACCGTAATCTGCCAAACGGTGTCTAAGTTAGGATACA 2340      2350      2360      2370      2380      2390      2400      2410      2420      2430      2440      2450
          *         *         *         *         *         *         *         *         *         *         *         *
AAGTCAATAATTCACGTTCCTCAAGCGGTGCCATTAATGAAATCTGCGTTCGATCCAAATTAGTAAAGGAGCTAGTTCTTCTGAGTTTGGCAGTGGCTCGCTAGGCGG
TTCAGTTATAAGTGCAAGGAGTTCGCCACGGTAATTACTTTATGCTTTAGACGCAAGCTAGGTTTAATCATTCCTCGATCAAGAAGACTCAAACCGTCACCGAGCGATCCGCC 2460      2470      2480      2490      2500      2510      2520      2530      2540      2550      2560      2570
          *         *         *         *         *         *         *         *         *         *         *         *
TTCGGTGCAATTCCGTACCAAAGAGGTAAGCGACATTATTAAGCCAGGGCAATCTTGGGACTAGATACCAGGCTACGACAAAAGTGCCTACAGCAGCAAAAATCAACAATGGTAAACTCACTTGCTTT
AAGCCACGTTAAGGCATGGTTTCTCCATTCGCTGTAATAATTCGGTCCCGTTAGAACCCTGATCTATGGTTTCACGGATGTCGTCGTTTTAGTTGTTACCAATTTGAGTGAACGAAA 2580      2590      2600      2610      2620      2630      2640      2650      2660      2670      2680      2690
          *         *         *         *         *         *         *         *         *         *         *         *
TGCGGGTACTCACAATGGCTTTGAGTCTCTTGTGATTTACACTCACCGTGATGGTAAGGAAGCTCATAAGGATGCAGAAAGCCGTTCTAAGTATTCAGAGAGTGGATCTAAG
ACGCCCATGAGTGTTACCGAAACTCAGAGAACTAAATGTGAGTGGCACTCCTTCCTTCGCAAGATTCCTACGTCTTCGAGTATTCTCATAAGTCTCCACCTAGATTC

*
CTT
GAA
```

```
          1090         1100         1110         1120         1130         1140         1150         1160         1170
            *            *            *            *            *            *            *            *            *
     GAT GCA ACT AAA ATT GAT TTA AAT ACC CAA TTT AAT GCT AAA GAA CTC AAC AAT TTT GGT GAT GCC AAT TCT GTT TTA ATT GAT GGA CAA AAA
     CTA CGT TGA TTT TAA CTA AAT TGG GTT AAA TTA CGA TTT CTT GAG TTG TTA AAA CCA CTA CGG AGA CAA AAT TAA CCT GTT TTT
     Asp Ala Thr Lys Ile Asp Leu Asn Thr Gln Phe Asn Ala Lys Glu Leu Asn Asn Phe Gly Asp Ala Asn Ser Val Leu Ile Asp Gly Gln Lys>

1180         1190         1200         1210         1220         1230         1240         1250         1260
            *            *            *            *            *            *            *            *            *
     ATA GAT CTA GCA GGT GTC AAT TTT AAA AAT AGT AAA ACG GTT GAA CTT AAA ATC AAC GGC ACA ATG TAC CAT CGG GTA GCT TGT AGT AAT CTG
     TAT CTA GAT CGT CCA CAG TTA AAA TTT TTA TCA TTT TGC CAA CTT TAG TTG TTG CCG TGT TAC ATG GTA GCC CAT CGA ACA TCA TTA GAC
     Ile Asp Leu Ala Gly Val Asn Phe Lys Asn Ser Lys Thr Val Glu Leu Lys Ile Asn Gly Thr Met Tyr His Arg Val Ala Cys Ser Asn Leu>

1270         1280         1290         1300         1310         1320         1330         1340         1350
            *            *            *            *            *            *            *            *            *
     GAA TAT ATG AAA TTT GGT CAA TTG TGG CAA AAA GAG GGC AAA CAA CAA GTT AAA TTT GAT AAT AGT TTA TTC CTA CAA GGT GAA CGT GCA CGT
     CTT ATA TAC TTT AAA CCA GTT AAC ACC GTT TTT CTC CCG TTT GTT CAA TTT AAA CTA TCA AAT AAG GAT AAG TTC CAA GGT CCA CTT GCA CGT
     Glu Tyr Met Lys Phe Gly Gln Leu Trp Gln Lys Glu Gly Lys Gln Gln Val Lys Phe Asp Asn Ser Leu Phe Leu Gln Gly Glu Arg Ala>

1360         1370         1380         1390         1400         1410         1420         1430         1440
            *            *            *            *            *            *            *            *            *
     ACG GAT AAA ATG CCC GCA GGA GGT TAT AAG AAC TTG GAT GTT GGA ACT CTC GTA TCT AAA GGG ACG AAC TGG ACC TAT ATA GCG GAA GCA
     TGC CTA TTT TAC GGG CGT CCA CTT CAA TTC TTG AAC CTA CAA CCT TGA GAG CAT AGA TTT CCC TGC TTG ACC TGC CGC TTC GGT
     Thr Asp Lys Met Pro Ala Gly Gly Tyr Lys Asn Leu Asp Val Gly Thr Leu Val Ser Lys Gly Thr Asn Trp Thr Tyr Ile Ala Glu Ala>

1450         1460         1470         1480         1490         1500         1510         1520         1530
            *            *            *            *            *            *            *            *            *
     GAT AAT CGA GAA TCG GGC TAT CGC ACT GAA TTT AGT GAT GTT GAT CTA AAA TCA AAA GAA AAA AAC GTA AAA GGT TAC TTA TTT GAT AAA GGT
     CTA TTA GCT CTT AGC CCG ATA GCG TGA CTT AAA TCA CTA CAA TTA AGT TTT CAT TTT TTG CAT TTT CCA ATG AAT AAA CTA TTT CCG CCA
     Asp Asn Arg Glu Ser Gly Tyr Arg Thr Glu Phe Asp Val Asp Leu Lys Ser Lys Glu Lys Asn Val Lys Gly Leu Phe Asp Lys Gly>
```

FIG. 2D

```
TF37   - MHFKLNPYALAFTSLFLVACSGGKGSFDLEDVRPNQTAKAEKATTSYQDE  -50
         ::::::::::::::::::::::::::::::::::::: :    :  ::
TF205  - MHFKLNPYALAFTSLFLVACSGGKGSFDLEDVRPNKTTGVSKEE--YKDV  -48

TF37   - ETKKKTKEELDKLMEPALGYETQILRRNKAPKTETGEKRNERVVELSEDK  -100
         :: :: ::  : :::::::::
TF205  - ETAKKEKEQLGELMEPALGYVVKVP-------------------------  -73

TF37   - ITKLYQESVEIIPHLDELNGKTTSNDVYHSHDSKRLD-------------  -137
                                  :    :   :
TF205  - ---------------------VSSFENKKVDISDIEVITNGNLD  -96

TF37   - -----------------KNRDLKYVRSGYVYDG---SFNEIRRNDSGFH  -166
                           :   : :::::::: ::    ::
TF205  - DVPYKANSSKYNYPDIKTKDSSLQYVRSGYVIDGEHSGSNE--------  -137

TF37   - VFKQGIDGYVYYLGVTPSKELPKGKVISYKGTWDFVSNINLEREIDGFDT  -216
         :::::  :   : ::::   :  :  ::: :: ::
TF205  - ------KGYVYYKGNSPAKELPVNQLLTYTGSWDFTSNANL--------  -172

TF37   - SGDGKNVSATSITETVNRDHKVGEKLGDNEVKGVAH-------------  -252
                                :   :
TF205  - -------------------------NNEEGRPNYLNDDYYTKFIGKR  -194

TF37   - ---------------SSEFAVDFDNKKLTGSLYRNGYINRNKAQEVTKRY  -287
                        :  : :::   ::  ::   :               :
TF205  - VGLVSGDAKPAKHKYTSQFEVDFATKKMTGKL----------SDKEKTIY  -234

TF37   - SIEADIAGNRFRGKAKA-------EKAGDPIFTDSNYLEGGFYGPKAEEM  -330
         ::: ::::  : :           ::  :::::::::::::::
TF205  - TVNADIRGNRFTGAATASDKNKGKGESYNFFSADSQSLEGGFYGPKAEEM  -284

TF37   - AGKFFTNNKSLFAVFAAKSENGETTTERIIDATKIDLTQFNAKELNNFGD  -380
         :::: :  : ::::::: ::          : :::::: :: : ::::::
TF205  - AGKFVANDKSLFAVFSAKHNGSNVNTVRIIDASKIDLTNFSISELNNFGD  -334

TF37   - ASVLIIDGQKIDLAGVNFKNSKTVEINGKTMVAVACCSNLEYMKFGQLWQ  -430
         :::::::: ::  :::  ::  :  : ::::::::::::::::::::::
TF205  - ASVLIIDGKKIKLAGSGFTNKHTIEINGKTMVAVACCSNLEYMKFGQLWQ  -384

TF37   - KEGKQQVKDNSLFLQGERTATDKMPAGGNYKYVGTWDALVSKGTNWIAEA  -480
         ::::::::::::::::::  ::::::: :::::: :: :::::  :: :
TF205  - QAEGGKPENNSLFLQGERTATDKMPKGGNYKYIGTWDAQVSKENNWVATA  -434

TF37   - DNNRESGYRTEFDVNFSDKKVNGKLFDKGGVNPVFTVDATINGNGFIGSA  -530
         :   : :::::::::  :::  :: :::::::::::::::  : :: :
TF205  - DDDRKAGYRTEFDVDFGNKNLSGKLFDKNGVNPVFTVDAKIDGNGFTGKA  -484

TF37   - KTSDSGFALDAGSSQHGNAVFSDIKVNGGFYGPTAGELGGQFHHKSDNGS  -580
         ::::  :::: ::: :  : : : ::::::::::: ::::::::::  ::
TF205  - KTSDEGFALDSGSSRYENVKFNDVAVSGGFYGPTAAELGGQFHHKSENGS  -534

TF37   - VGAVFGAKRQIEK  -593
         ::::::::: :
TF205  - VGAVFGAKQQVKK  -547         FIG. 3
```

```
CTGTTATAGA TCTAGGAAAAA GCAAGTTTAG GTTTGGACAT TATCTCTGGT
           BglII
TTACTTTCTG GAGCATCTGC AGGTCTCATT TTAGCAGATA AAGAGGCTTC

AACAGAAAAG AAAGCTGCCG CAGGTGTAGA ATTTGCTAAC CAAATTATAG

GTAATGTAAC AAAAGCGGGTC TCATCTTACA TTCTTGCCCA ACGAGTCGCT

TCAGGTTTGT CTTCAACTGG TCCTGTCGCT GCATTAATCG CATCTACAGT

TGCACTAGCT GTTAG
```

FIG. 4

BamHI ----//----|—<————————|CTTAATGATA TAACAGCGGT CAAATTCTAA
                  1201 bp repeat AATCTTTTGC AATGTGCAAC TTTTATTAGG ATT -----//------       cytA-//-

TCTAGATGGA AAAGGTTTGT CTTTAACATC ATGGTTAATC GCAGCAAAAT CATTAGATTT
 XbaI
AAAAGCAAAG GCTATTAATA AAGCCGTTGA GCGTTTACCT TTTGTTAATT TACCTGCACT

TATCTGGAGG GAAGATGGAA AACATTTTAT CTTAGTAAAG ATAGATAAAG ATAAAAAACG

CTATTTAAC|—<————————|---//---BglII
          1201 bp repeat

FIG. 14

```
diverging sequence
    |
    T-G-T-A-G-A-A-A-A-T-C-A-A-A-C-C-T-A-A-T-C-T-G-A-C-A┐
    | | | | | | | | | | | | | | | | | | | | | | | | |  repeat sequence
    A-C-A-T-C-T-T-C-T-A-G-T-C-T-G-A-A-C-T-A-G-A-C-T-G-T┘
    |
diverging sequence
```

FIG. 15

```
   1 GGATCCTGTT CTTGGTGAAA GTGTGGAACT TAAAGTTAAC TTATGTTTAG AGAAAAAAGG
     BamHI
  61 ATGGTATCTA GAGCAAGGTC CAGTGTGTGA AGAAAAATAC GTATGGAATG AACCGGAATG
 121 TATTAAATGG CGAGCAAAAT ATAGTAAGCC AAATGTGCAA CCTTGGGGAT AATAGTCATT
 181 TAAGTGTTTT AAAAATTTAA TTTCAGAAAT TTGTAATGGA TACAATGAAT ACAGAAAATA
 241 ATTAATGTTT AAAATCAAGC ACTAAATGAT TTTGTAATGG CACTTTAGCT GGGGTTATAT
 301 GAAGTAAATT CTTAATGTGT AGAAAATCAA ACCTAATCTG ACAGTTCCCG TTTAAAATTA
                                  inverted repeat
 361 CCGTGTCTGT CAGATTAATT TGAGCTTAAA TTCTTTTCTG CCCAAATCCG TTTTCCATCA
                         *** <----- end of open reading frame
 421 AGTAATGTTG CCATCGGTGT TCTGCCACAG CACACTTTTC CTTGATGTGT TCGATGGTGA
 481 TTATAATACA TTAACCACTC ATCTAAATCA GCTTGTAATG TCGCTAAATC CGTATATATT
 541 TTCTTCCTAA ATGCGACTTG GTAAAATTCT TGTAAGATAG TCTTATGAAA ACGTTCACAG
 601 ATACCATTCG TCTGTGGATG CTTCACTTTC GTTTTAGTAT GCTCTATGTC ATTTATCGCT
 661 AAATAAAGCT CATAATCGTG ATTTTCCACT TTGCCACAAT ATTCACTGCC ACGGTCGGTG
 721 AGAATACGCA ACATCGGTAA TCCTTGGGCT TCAAAGAACG GCAGTACTTT ATCATTGAGC
 781 ATATCTGCAG CGGCAATTGC GGTTTTCATT GTGTAGAGCT TTGCAAAAGC AACCTTACTA
 841 TAAGTATCAA CAAATGTTTG CTGATAAATG CGTCCAACAC CTTTTAAATT ACCTACATAA
 901 AAGGTATCTT GTGAACCTAA ATAGCCCGGA TGAGCGGTTT CAATTTCTCC ACTCGATATA
 961 TCATCCTCTT TCTTACGTTC TAGGGCTTGG ACTTGACTTT CATTTAGAAT AATGCCTTTC
1021 TCAGCCACTT CTTTCTCTAG TGCATTTAAA CGCTGTTTAA AGTTAGTAAG ATTATGACGT
1081 AGCCAAATGG AACGAACACC ACCGGCTGAA ACAAACACAC CTTGCTTGCG AAGTTCGTTA
1141 CTCACTCGAA CTTGTCCGTA AGCTGGAAAA TCTAGAGCAA ATTTTACAAC AGCTTGCTCA
1201 ATGTGCTCGT CTACTCGATT TTTGATATTC GGTACCCGAC GAGTTTGCTT AACTAATGCT
                                             KpnI
1261 TCAACACCGC CTTGCGCTAC GGCTTGTTGA TAGCGATAGA ATGTATCTCG GCTCATTCCC
1321 ATCGCTTTAC AAGCTTGAGA AATGTTTCCG AGTTCTTCTG CTAAATTGAG TAAACCGGTC
1381 TTGTGTTTAA TGAGCGGATT GTTAGAATAA AACATGAGAG TTTCCTTTTT TGTTTAGATT
          start of open reading frame <--- MET        SD
1441 GAATTTTAGA CACTCATATT CTAAACGGGA AACTCTCATT TTTATAATGA TTTGTCAGAT
1501 CAAGTCTGAT CTTCTACAAA TATTATCCCC ATTTATGGAG TTCGTCTTTT AGATGAACTC
     inverted repeat
1561 CTATTGTTTA TAATTCGATA AAATTAGCTT TCTCACAGCA ACTCAGCAAT GGGTTGCTTT
1621 TTTATTTGAC AGAAAAACAA CGTAGATCT
                                BglII
```

FIG. 16

ACTINOBACILLUS PLEUROPNEUMONIAE TRANSFERRIN BINDING PROTEINS AND USES THEREOF

CROSS-REFERENCE TO RELATED APPLICATION

This application is a continuation of U.S. patent application Ser. No. 07/961,522, filed Oct. 15, 1992, now U.S. Pat. No. 5,417,971, which is a continuation-in-part of U.S. patent application Ser. No. 07/780,912, filed Oct. 22, 1991, now abandoned, from which priority is claimed under 35 USC §120 and which are hereby incorporated by reference in their entirety.

TECHNICAL FIELD

The instant invention relates generally to the prevention of disease in swine. More particularly, the present invention relates to subunit vaccines for *Actinobacillus pleuropneumoniae.*

BACKGROUND

*Actinobacillus* (formerly *Haemophilus*) *pleuropneumoniae* is a highly infectious porcine respiratory tract pathogen that causes porcine pleuropneumonia. Infected animals develop acute fibrinous pneumonia which leads to death or chronic lung lesions and reduced growth rates. Infection is transmitted by contact or aerosol and the morbidity in susceptible groups can approach 100%. Persistence of the pathogen in clinically healthy pigs also poses a constant threat of transmitting disease to previously uninfected herds.

The rapid onset and severity of the disease often causes losses before antibiotic therapy can become effective. Presently available vaccines are generally composed of chemically inactivated bacteria combined with oil adjuvants. However, whole cell bacterins and surface protein extracts often contain immunosuppressive components which make pigs more susceptible to infection. Furthermore, these vaccines may reduce mortality but do not reduce the number of chronic carriers in a herd.

There are at least 12 recognized serotypes of *A. pleuropneumoniae* with the most common in North America being serotypes 1, 5 and 7. Differences among serotypes generally coincide with variations in the electrophoretic mobility of outer membrane proteins and enzymes thus indicating a clonal origin of isolates from the same serotype. This antigenic variety has made the development of a successful vaccination strategy difficult. Protection after parenteral immunization with a killed bacterin or cell free extract is generally serotype specific and does not prevent chronic or latent infection. Higgins, R., et al., *Can. Vet. J.* (1985) 26:86–89; Macinnes, J. I. and Rosendal, S., *Infect. Immun.* (1987) 55:1626–1634. Thus, it would be useful to develop vaccines which protect against both death and chronicity and do not have immunosuppressive properties. One method by which this may be accomplished is to develop subunit vaccines composed of specific proteins in pure or semipure form.

*A. pleuropneumoniae* strains produce several cytolysins. See, e.g. Rycroft, A. N., et al., *J. Gen. Microbiol.* (1991) 137:561–568 (describing a 120 kDa cytolysin from *A. pleuropneumoniae*); Chang, Y. F., et al., *DNA* (1989) 8:635–647 (describing a cytolysin isolated from *A. pleuropneumoniae* serotype 5); Kamp, E. M., et al., Abstr. *CRWAD* (1990) 1990:270 (describing the presence of 103, 105 and 120 kDa cytolysins in *A. pleuropneumoniae* strains) and Welch, R. A., *Mol. Microbiol.* (1991) 5:521–528 (reviewing cytolysins of gram negative bacteria including cytolysins from *A. pleuropneumoniae*). One of these cytolysins appears to be homologous to the alphahemolysin of *E. coli* and another to the leukotoxin of *Pasteurella haemolytica.* Welch, R. A., *Mol. Microbiol.* (1991) 5:521–528. These proteins have a molecular mass of approximately 105 kDa and are protective in mouse and pig animal models against challenge with the homologous serotype. However, cross-serotype protection is limited at best (Higgins, R., et al., *Can. J. Vet.* (1985) 26:86–89; Macinnes, J. I., et al., *Infect. Immun.* (1987) 55:1626–1634. The genes for two of these proteins have been cloned and expressed in *E. coli* and their nucleotide sequence determined. Chang, Y. F., et al., *J. Bacteriol.* (1991) 173:5151–5158 (describing the nucleotide sequence for an *A. pleuropneumoniae* serotype 5 cytolysin); and Frey, J., et al., *Infect. Immun.* (1991) 59:3026–3032 (describing the nucleotide sequence for an *A. pleuropneumoniae* serotype 1 cytolysin).

Transferrins are serum glycoproteins that function to transport iron from the intestine where it is absorbed, and liver, where it is stored, to other tissues of the body. Cell surface receptors bind ferrotransferrin (transferrin with iron) and the complex enters the cell by endocytosis. *A. pleuropneumoniae,* under iron restricted growth conditions, can use porcine transferrin as its sole iron source, but it cannot utilize bovine or human transferrin (Gonzalez, G. C., et al., *Mol. Microbiol.* (1990) 4:1173–1179; Morton, D. J., and Williams, P., *J. Gen. Microbiol.* (1990) 136:927–933). The ability of other microorganisms to bind and utilize transferrin as a sole iron source as well as the correlation between virulence and the ability to scavenge iron from the host has been shown (Archibald, F. S., and DeVoe, I. W., *FEMS Microbiol. Lett.* (1979) 6:159–162; Archibald, F. S., and DeVoe, I. W., *Infect. Immun.* (1980) 27:322–334; Herrington, D. A., and Sparling, F. P., *Infect. Immun.* (1985) 48:248–251; Weinberg, E. D., *Microbiol. Rev.* (1978) 42:45–66).

It has been found that *A. pleuropneumoniae* possesses several outer membrane proteins which are expressed only under iron limiting growth conditions (Deneer, H. G., and Potter, A. A., *Infect. Immun.* (1989) 57:798–804). Three of these proteins have been isolated from A. pleuropneumoniae serotypes 1, 2 and 7 using affinity chromatography. These proteins have molecular masses of 105, 76 and 56 kDa. (Gonzalez, G. C., et al., *Mol. Microbiol.* (1990) 4:1173–1179). The 105 and 56 kDa proteins have been designated porcine transferrin binding protein 1 (pTfBP1) and porcine transferrin binding protein 2 (pTfBP2), respectively. (Gonzalez, G. C., et al., *Mol. Microbiol.* (1990) 4:1173–1179). At least one of these proteins has been shown to bind porcine transferrin but not transferrin from other species (Gonzalez, G. C., et al., *Mol. Microbiol.* (1990) 4:1173–1179). It is likely that one of these proteins, either alone or in combination with other iron regulated outer membrane proteins, is involved in the transport of iron. The protective capacity of these proteins has not heretofore been demonstrated.

DISCLOSURE OF THE INVENTION

The instant invention is based on the discovery of novel subunit antigens from *A. pleuropneumoniae* which show protective capability in pigs.

Accordingly, in one embodiment, the subject invention is directed to a vaccine composition comprising a pharmaceutically acceptable vehicle and a subunit antigen composition. The subunit antigen composition includes at least one amino acid sequence substantially homologous and functionally equivalent to an immunogenic polypeptide of an *Actinobacillus pleuropneumoniae* protein or an immunogenic fragment thereof. The immunogenic protein is selected from the group consisting of *Actinobacillus pleuropneumoniae* transferrin binding protein, *Actinobacillus pleuropneumoniae* cytolysin and *Actinobacillus pleuropneumoniae* APP4.

In other embodiments, the instant invention is directed to a nucleotide sequences encoding *Actinobacillus pleuropneumoniae* transferrin binding proteins and nucleotide sequences encoding *Actinobacillus pleuropneumoniae* APP4 proteins, or proteins substantially homologous and functionally equivalent thereto.

In yet other embodiments, the subject invention is directed to DNA constructs comprising an expression cassette comprised of:

(a) a DNA coding sequence for a polypeptide containing at least one epitope of an *Actinobacillus pleuropneumoniae* transferrin binding protein; and (b) control sequences that are operably linked to the coding sequence whereby the coding sequence can be transcribed and translated in a host cell, and at least one of the control sequences is heterologous to the coding sequence.

In another embodiment, the subject invention is directed to a DNA construct comprising an expression cassette comprised of:

(a) a DNA coding sequence for a polypeptide containing at least one epitope of an *Actinobacillus pleuropneumoniae* cytolysin; and (b) control sequences that are operably linked to the coding sequence whereby the coding sequence can be transcribed and translated in a host cell, and at least one of the control sequences is heterologous to said coding sequence.

In still another embodiment, the invention is directed to a DNA construct comprising an expression cassette comprised of:

(a) a DNA coding sequence for a polypeptide containing at least one epitope of an *Actinobacillus pleuropneumoniae* APP4; and (b) control sequences that are operably linked to the coding sequence whereby the coding sequence can be transcribed and translated in a host cell, and at least one of the control sequences is heterologous to the coding sequence.

In still further embodiments, the instant invention is directed to expression cassettes comprising the DNA constructs, host cells transformed with these expression cassettes, and methods of recombinantly producing the subject *Actinobacillus pleuropneumoniae* proteins.

In another embodiment, the subject invention is directed to methods of treating or preventing pneumonia in swine comprising administering to the swine a therapeutically effective amount of a vaccine composition as described above.

In still other embodiments, the invention is directed to isolated and purified *Actinobacillus pleuropneumoniae* serotype 7 60 kDa transferrin binding protein, serotype 5 62 kDa transferrin binding protein, serotype 1 65 kDa transferrin binding protein and serotypes 1 and 5 APP4.

These and other embodiments of the present invention will readily occur to those of ordinary skill in the art in view of the disclosure herein.

BRIEF DESCRIPTION OF THE FIGURES

Figure 1B:
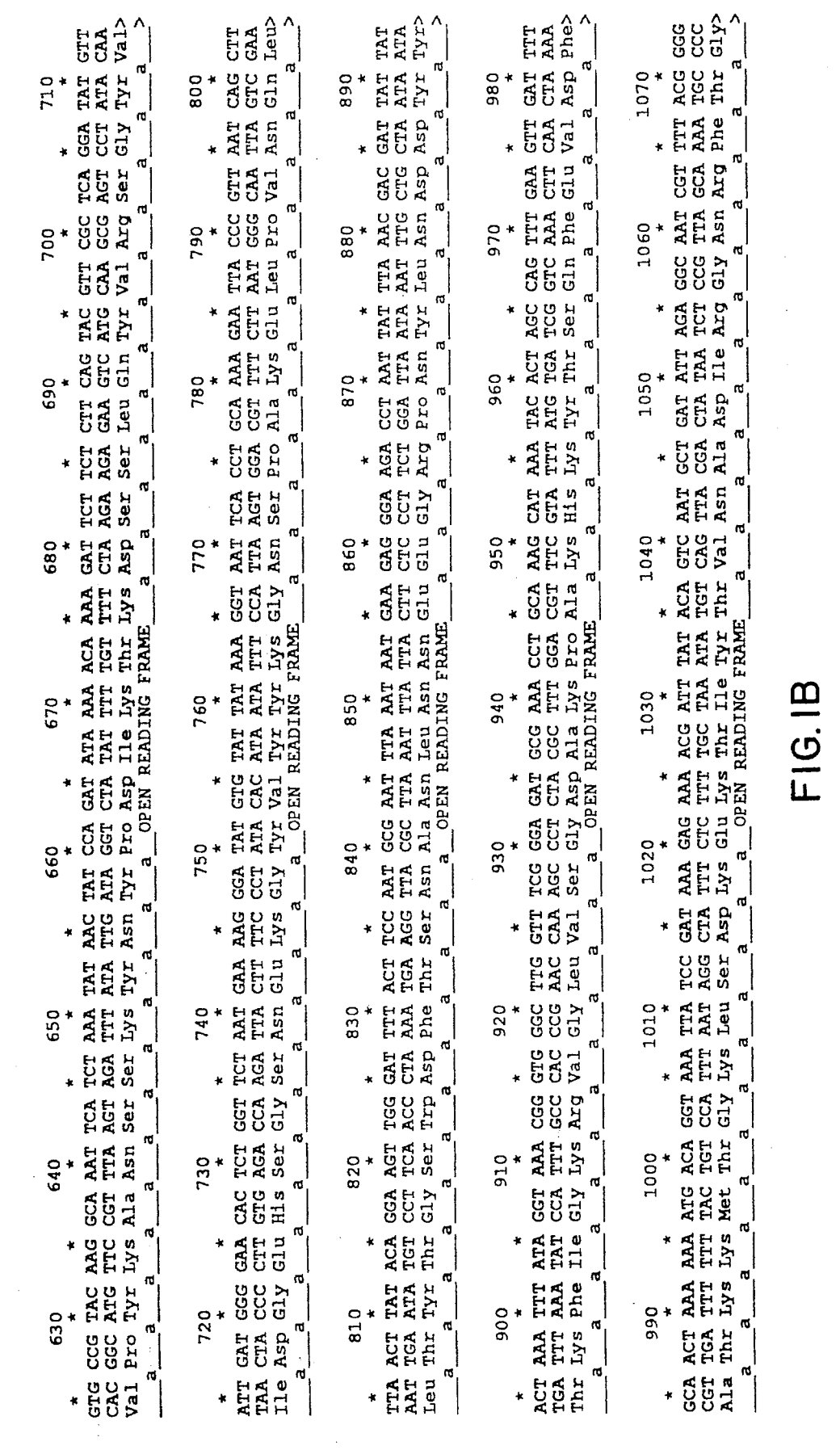

FIGS. 1A–1E (SEQ ID NOS:1 and 2) depict the nucleotide sequence and deduced amino acid sequence of *A. pleuropneumoniae* serotype 7 60 kDa transferrin binding protein as well as the nucleotide sequence for the flanking regions.

Figure 2A:
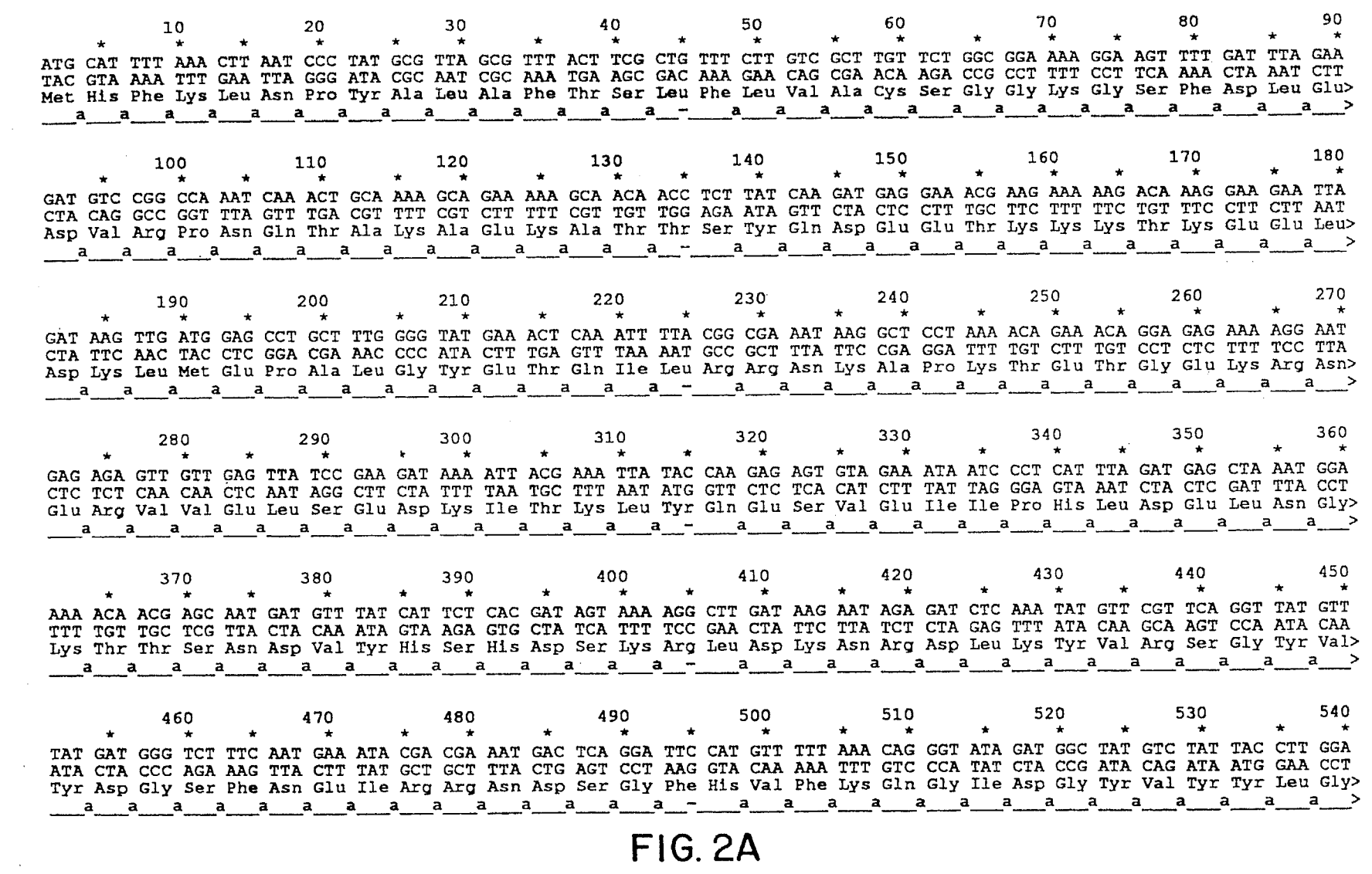
Figure 2B:
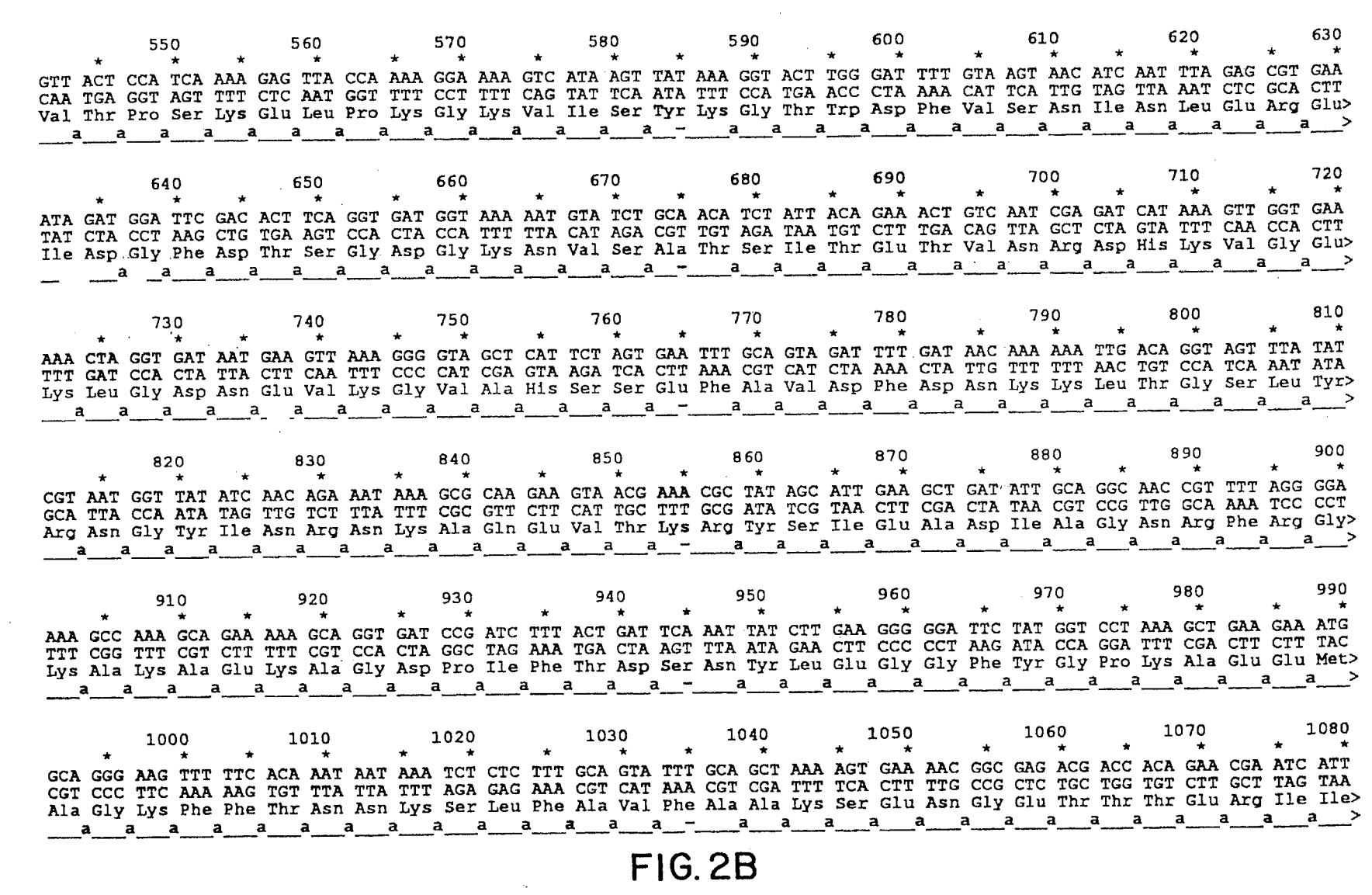
Figure 2D:
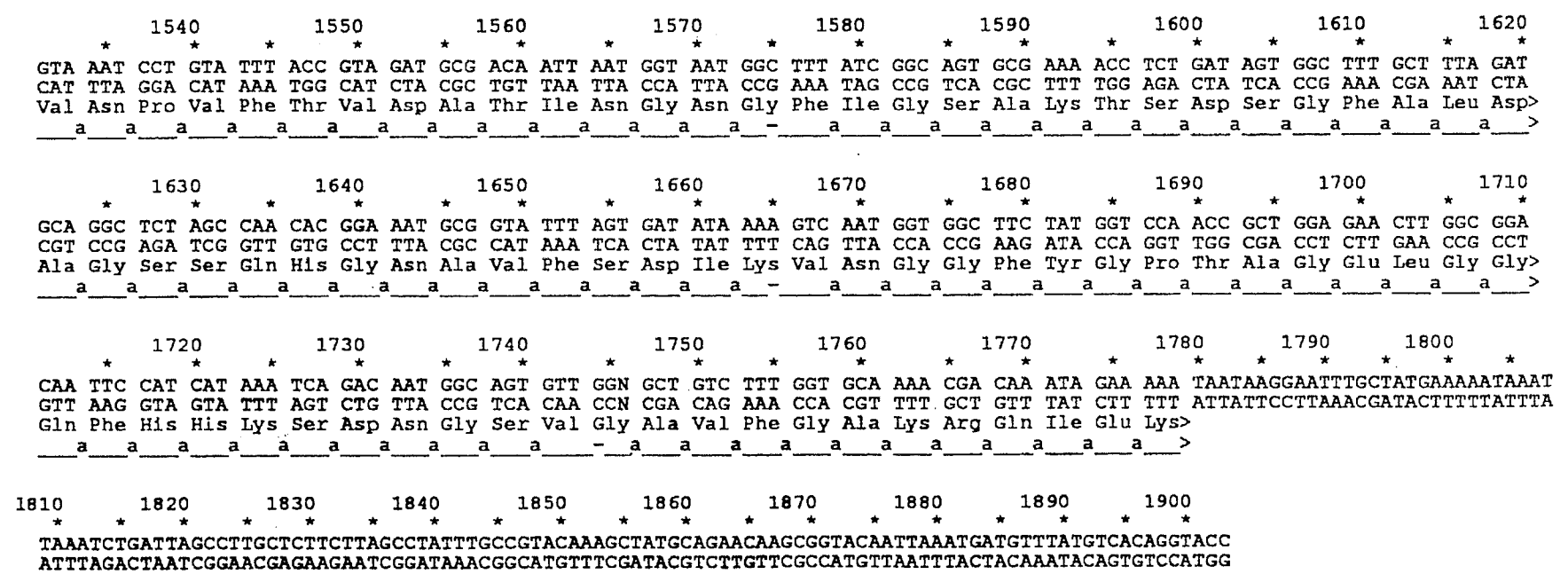

FIGS. 2A–2D (SEQ ID NOS:3 and 4) show the nucleotide sequence and deduced amino acid sequence of *A. pleuropneumoniae* serotype 1 65 kDa transferrin binding protein as well as the nucleotide sequence for the flanking regions.

FIG. 3 is a comparison of the amino acid sequences of *A. pleuropneumoniae* serotype 7 60 kDa transferrin binding protein (designated "TF205" therein) (SEQ ID NO:6) and the *A. pleuropneumoniae* serotype 1 65 kDa transferrin binding protein (designated "TF37" therein) (SEQ ID NO:5). Dots indicate positions of identity.

FIG. 4 (SEQ ID NO:7) shows the partial nucleotide sequence of *A. pleuropneumoniae* serotype 7, 103 kDa cytolysin. The BglII site is the fusion point between the vector pGH432 lacI and the *A. pleuropneumoniae* derived sequence.

FIGS. 12A–13B shows the means of clinical response (12A) and body temperature (12B) of pigs challenged with *A. pleuropneumoniae* serotype 7 in trial 1 of Example 6. The numbers on top of the bars represent the number of animals from which the values were obtained.

FIGS. 13A–13B show the means of clinical response (13A) and body temperature (13B) of pigs challenged with *A. pleuropneumoniae* serotype 7 in trial 2 of Example 6. The numbers on top of the bars represent the number of animals from which the values were obtained.

FIG. 14 (SEQ ID NO:9) shows the nucleotide sequence of the flanking regions of the repeats on λCY76/5. cytA marks the position of the cytA gene, and the sequence at the XbaI site and upstream is identical to that described by Chang, Y. F., et al., *DNA* (1989) 8:635–647.

FIG. 15 (SEQ ID NOS:10 and 11) depicts the nucleotide sequence of the inverted repeats of FIG. 14 located on either end of the direct repeats. Complementary bases are connected with a vertical dash.

FIG. 16 (SEQ ID NO:8) depicts the nucleotide sequence of the BamHI-BglII fragment of λCY76Δ1/1. BamHI, KpnI, and BglII indicate the position of the restriction enzyme sites. The position and direction of the open reading frame is indicated by "MET" and "***". "SD" marks the Shine-Dalgarno consensus sequence. The ends of the repeat are comprised of 26 bp long inverted repeats also emphasized by bold print.

DETAILED DESCRIPTION

Figure 5:
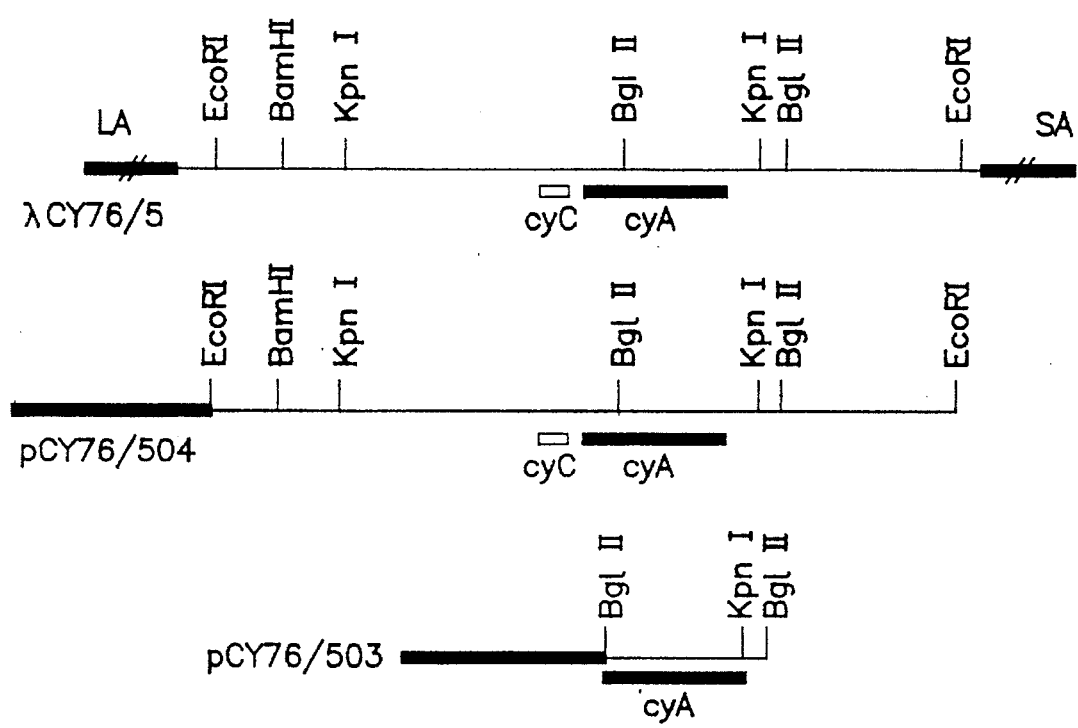
FIG. 5 shows restriction endonuclease cleavage maps of *A. pleuropneumoniae* serotype 7 cytolysin clones. The cyA region contains the structural gene for the cytolysin while cyC codes for an activator protein.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications and publications cited herein, whether supra or infra, are hereby incorporated by reference in their entirety.

A. Definitions

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen."

By "subunit antigen" is meant an antigen entity separate and discrete from a whole bacterium (live or killed). Thus, an antigen contained in a cell free extract would constitute a "subunit antigen" as would a substantially purified antigen.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T ,5 cells directed specifically to an antigen or antigens included in the composition or vaccine of interest.

The terms "immunogenic polypeptide" and "immunogenic amino acid sequence" refer to a polypeptide or amino acid sequence, respectively, which elicits antibodies that neutralize bacterial infectivity, and/or mediate antibody-complement or antibody dependent cell cytotoxicity to provide protection of an immunized host. An "immunogenic polypeptide" as used herein, includes the full length (or near full length) sequence of the desired *A. pleuropneumoniae* protein or an immunogenic fragment thereof. By "immunogenic fragment" is meant a fragment of a polypeptide which includes one or more epitopes and thus elicits antibodies that neutralize bacterial infectivity, and/or mediate antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the *A. pleuropneumoniae* subunit antigens.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native transferrin binding protein" "native cytolysin" or "native APP4" would include naturally occurring transferrin binding protein, cytolysin or APP4, respectively, and fragments of these proteins. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" or a "nucleotide sequence encoding" a particular protein, is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence-in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the subject protein is one that will elicit an immunological response, as defined above, equivalent to the specified *A. pleuropneumoniae* immunogenic polypeptide.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms of the disease of interest (therapy).

B. General Methods

Central to the instant invention is the discovery of certain *A. pleuropneumoniae* proteins able to elicit an immune response in an animal to which they are administered. The antigens, or immunogenic fragments thereof, are provided in subunit vaccine compositions and thus problems inherent in prior vaccine compositions, such as localized and systemic side reactions, as well as the inability to protect against chronic disease, are avoided. The vaccine compositions can be used to treat or prevent *A. pleuropneumoniae* induced respiratory diseases in swine such as porcine pleuropneumonia. The antigens or antibodies thereto can also be used as diagnostic reagents to detect the presence of *A. pleuropneumoniae* infection in a subject. Similarly, the genes encoding the subunit antigens can be cloned and used to design probes for the detection of *A. pleuropneumoniae* in tissue samples as well as for the detection of homologous genes in other bacterial strains. The subunit antigens are conveniently produced by recombinant techniques, as described herein. The proteins of interest are produced in high amounts in transformants, do not require extensive purification or processing, and do not cause lesions at the injection site or other ill effects.

It has now been found that *A. pleuropneumoniae* possesses proteins able to bind transferrin. Specifically, two transferrin binding proteins have been identified in cell free extracts from *A. pleuropneumoniae* serotype 7. These proteins have molecular masses of approximately 60 kDa and 100 kDa, respectively, as determined by SDS PAGE. The 100 kDa protein is seen only in cells grown under iron restriction and appears to be present in substantial amounts in the outer membrane. The 60 kDa protein is detectable in whole cell lysates and culture supernatants from bacteria grown under iron restricted conditions. This protein is not seen in outer membranes prepared by SDS solubilization. The protein does not appear to be expressed under conditions of heat, ethanol, or oxidative stress. The 60 kDa protein, when separated by nondenaturing PAGE, binds alkaline phosphatase labeled porcine transferrin and exhibits species-specific binding in competitive ELISAs. Congo Red and hemin are able to bind this protein, thereby inhibiting the transferrin binding activity. Southern and Western blot analysis shows that this, or a related protein is also likely present in *A. pleuropneumoniae* serotypes 2, 3, 4, 8, 9, 10 and 11 in addition to serotype 7. A functionally related protein is present in serotypes 1, 5 and 12. The 60 kDa tranferrin binding protein is effective in protecting pigs against *A. opleuropneumoniae* infections. The presence of this protein in culture supernatants and its absence from purified outer membranes indicates that it is different from the iron regulated outer membrane proteins previously described by Deneer and Potter (Deneer, H. G., and Potter, A. A., *Infect. Immun.* (1989) 57:798–804).

The gene encoding the *A. pleuropneumoniae* serotype 7 60 kDa transferrin binding protein has been isolated and the sequence is depicted in FIGS. 1A–1E (SEQ ID NO:1). The nucleotide sequence including the structural gene and flanking regions consists of approximately 2696 base pairs. The open reading frame codes for a protein having approximately 547 amino acids. The putative amino acid sequence of the 60 kDa protein is also depicted in FIGS. 1A–1E (SEQ ID NOS:1 and 2). The recombinantly produced protein is able to protect pigs from subsequent challenge with *A. pleuropneumoniae*.

The gene encoding an *A. pleuropneumoniae* serotype 5 transferrin binding protein has also been identified and cloned. This gene was cloned by screening an *A. pleuropneunomiae* serotype 5 genomic library with DNA probes from a plasmid which encodes the serotype 7 60 kDa transferrin binding protein (thus suggesting at least partial homology to this protein). When transformed into *E. coli* HB101, the recombinant plasmid expressing the serotype 5 transferrin binding protein gene produced a polypeptide of approximately 62 kDa which reacted with convalescent serum from an *A. pleuropneumoniae* serotype 5-infected pig. The serotype 5 recombinant transferrin binding protein is also able to protect pigs from subsequent challenge with *A. pleuropneumoniae*, as described further below.

*A. pleuropneumoniae* serotype 1 has also been found to possess a protein which shows 58.3% homology with the serotype 7 60 kDa transferrin binding protein (FIG. 3; SEQ ID NOS: 5 and 6). The nucleotide sequence and deduced amino acid sequence of the serotype 1 transferrin binding protein is shown in FIGS. 2A–2D (SEQ ID NOS:3 and 4). The nucleotide sequence including the structural gene and flanking sequences consists of approximately 1903 base pairs. The open reading frame codes for a protein having about 593 amino acids. This protein has a molecular mass of approximately 65 kDa, as determined by SDS PAGE.

As is apparent, the transferrin binding proteins appear to perform the same function (iron scavenging) and exhibit homology between serotypes. Vaccination with one serotype does not always provide cross-protection against another serotype. However, when these transferrin binding proteins are combined with other subunit antigens, as described below, crossprotection against clinical symptoms becomes possible.

It has also been found that *A. pleuropneumoniae* serotype 7 possesses at least one cytolysin with protective capability. This cytolysin has a molecular mass of approximately 103 kDa, as determined by SDS-PAGE. The gene for this cytolysin has been cloned and a partial nucleotide sequence determined (FIG. 4) (SEQ ID NO:7). The partial sequence shows identity with part of the sequence determined for a cytolysin isolated from *A. pleuropneumoniae* serotype 5 (Chang, Y. F., et al., *DNA* (1989) 8:635–647). A carboxy-terminal fragment of this cytolysin, containing 70% of the protein, has been found protective in an experimental pig model.

Figure 6:
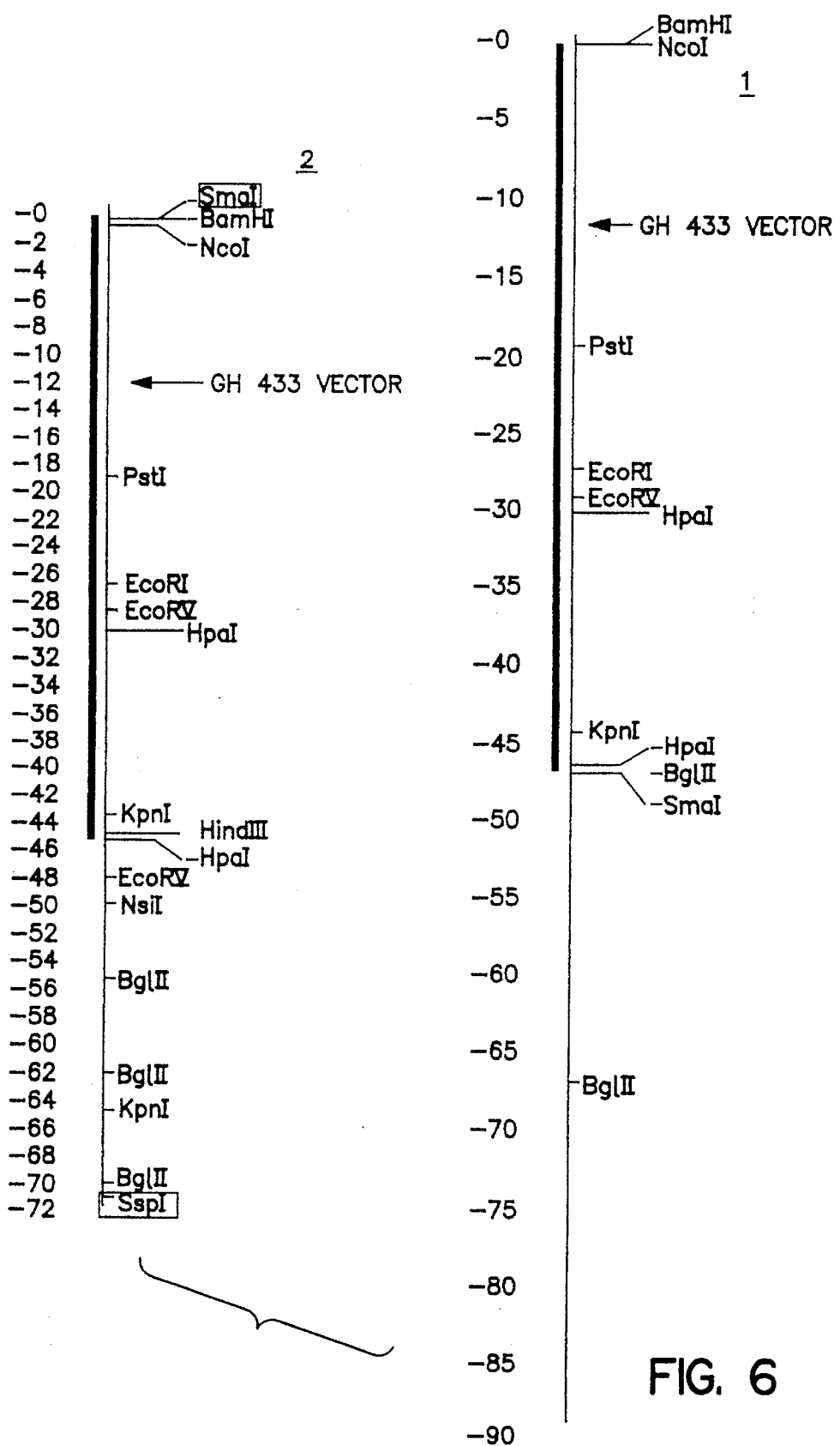
FIG. 6 shows restriction endonuclease cleavage maps for recombinant plasmids coding for *A. pleuropneumoniae* serotype 1 antigens. 6.1=rAPP 4, 6.2=pTF37/E1. The heavy line indicates the vector sequence and the coordinates are 0.01 Kb.

*A. pleuropneumoniae* serotypes also possess another protective protein, designated APP4, having a molecular mass of approximately 60 kDa. The genes encoding the proteins from serotypes 1 and 5, respectively, have been cloned. A restriction endonuclease cleavage map for a recombinant plasmid coding for recombinant *A. pleuropneumoniae* serotype 1 APP4 (rAPP4) is shown in FIG. 6.1. The gene coding a serotype 5 homolog of APP4 has been cloned from a library screened with DNA probes from the above plasmid. Both the serotype 5 and serotype 1 APP4 proteins afford protection in pigs from a subsequent challenge with *A. pleuropneumoniae*. Other APP4 proteins useful in the present vaccines include immunogenic APP4 polypeptides from additional *A. pleuropneumoniae* serotypes.

The described proteins, or immunogenic fragments thereof, or cell free extracts including the same, can be used either alone or in combination vaccine compositions. Such compositions can contain any combination of the described antigens, such as one or more *A. pleuropneumoniae* transferrin binding proteins and/or one or more *A. pleuropneumoniae* cytolysins and/or one or more *A. pleuropneumoniae* APP4s. Combination vaccines containing antigens from more than one serotype will provide broad spectrum protection. However, since it has been found that there is little cross-protection against heterologous serotypes when single antigens are used, for best results, serotype 7 antigens should be used for protection against *A. pleuropneumoniae* serotype 7 infections, serotype 1 antigens for protection against serotype 1 infections, serotype 5 antigens for protection against serotype 5 infections, and so on. Furthermore, based on genetic and antigenic differences of the 60 kDa proteins in strains studied, as well as the presence of two different cytolysins in certain serotypes (described further below), vaccines containing more than one of the cytolysins as well as the serotype specific 60 kDa proteins are particularly attractive for providing cross-protection against clinical symptoms.

If synthetic or recombinant proteins are employed, the subunit antigen can be a single polypeptide encoding several epitopes from just one of the *A. pleuropneumoniae* proteins or several epitopes from more than one of the proteins (e.g., a fusion protein). Synthetic and recombinant subunit antigens can also comprise two or more discrete polypeptides-encoding different epitopes.

The above described antigens can be produced by a variety of methods. Specifically, the antigens can be isolated directly from *A. pleuropneumoniae*, as described below. Alternatively, the antigens can be recombinantly produced as described herein. The proteins can also be synthesized, based on the described amino acid sequences, using techniques well known in the art.

For example, the antigens can be isolated from bacteria which express the same. This is generally accomplished by first preparing a crude extract which lacks cellular components and several extraneous proteins. The desired antigens can then be further purified i.e. by column chromatography, HPLC, immunoadsorbent techniques or other conventional methods well known in the art.

Purification of the above proteins as described herein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art. Furthermore, fragments of the proteins can be tested for biological activity and active fragments, as described above, used in compositions in lieu of the entire protein.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning:* Vol. I, supra; *Nucleic Acid Hybridization,* supra; *Oligonucleotide Synthesis,* supra; T. Maniatis et al., supra.

First, a DNA library is prepared. The library can consist of genomic DNA from *A. pleuropneumoniae.* Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization,* supra. The basic requirement is that hybridization conditions be of sufficient stringency so that selective hybridization occurs; i.e., hybridization is due to a sufficient degree of nucleic acid homology (e.g., at least about 65%), as opposed to nonspecific binding. Once a clone from the screened library has been identified by positive hybridization, it can be confirmed by restriction enzyme analysis and DNA sequencing that the particular insert contains a gene coding for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning:* Vols. I & II, supra; T. Maniatis et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Signal sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the antigens of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired antigen.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the protein of interest, or a fragment thereof, or an analog thereof. If the fragment or analog of the protein is used, it will include the amino acid sequence of an epitope which interacts with the immune system to immunize the animal to that and structurally similar epitopes. If combinations of the described antigens are used, the antigens can be administered together or provided as separate entities.

Prior to immunization, it may be desirable to increase the immunogenicity of the particular protein, or an analog of the protein, or particularly fragments of the protein. This can be accomplished in any one of several ways known to those of skill in the art. For example, the antigenic peptide may be administered linked to a carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Other suitable carriers for the proteins of the present invention include VP6 polypeptides of rotaviruses, or functional fragments thereof, as disclosed in U.S. Pat. No. 5,071,651, and incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

The novel proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK recombinant can be selected by culturing the cells in the presence of 5-bromodeoxyuridine and picking viral plaques resistant thereto.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The proteins can also be delivered using implanted mini-pumps, well known in the art.

Furthermore, the proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, 5 µg to 1 mg of active ingredient, more preferably 10 µg to 500 µg, of active ingredient, should be adequate to raise an immunological response when a dose of 1 to 2 ml of vaccine per animal is administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity to pneumonia.

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e. by injection (see International Publication No. WO/90/11092; and Wolff et al., *Science* (1990)

247:1465–1468). Liposome-mediated gene transfer can also be accomplished using known methods. See, e.g., Hazinski et al., *Am. J. Respir. Cell Mol. Biol.* (1991) 4:206–209; Brigham et al., *Am. J. Med. Sci.* (1989) 298:278–281; Canonico et al., *Clin. Res.* (1991) 39:219A; and Nabel et al., *Science* (1990) 249:1285–1288. Targeting agents, such as antibodies directed against surface antigens expressed on specific cell types, can be covalently conjugated to the liposomal surface so that the nucleic acid can be delivered to specific tissues and cells susceptible to *A. pleuropneumoniae* infection.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required under 35 USC § 112. The nucleic acid sequences of these plasmids, as well as the amino sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| pTF37/E1 (in *E. coli*) | 10/19/91 | 68823 |
| pTF205/E1 (in *E. coli*) | 10/19/91 | 68821 |
| pTF205/E2 (in *E. coli*) | 10/19/91 | 68822 |
| pTF213/E6 (in *E. coli*) | 10/8/92 | 69084 |
| pCY76/503 (in *E. coli*) | 10/19/91 | 68820 |
| #4-213-84 (in *E. coli*) | 10/8/92 | 69082 |
| prAPP4 (in *E. coli*) | 4/7/92 | 68955 |
| *A. pleuropneumoniae* serotype 1 strain AP37 | 10/19/91 | 55242 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli,* DNA polymerase I, Klenow fragment, and other biological reagents were purchased from commercial suppliers and used according to the manufacturers' directions. Double stranded DNA fragments were separated on agarose gels.

Bacterial Strains, Plasmids and Media

*A. pleuropneumoniae* serotype 7 strain AP205 was a Nebraska clinical isolate obtained from M. L. Chepok, Modern Veterinary Products, Omaha, Nebr. *A. pleuropneumoniae* serotype 1 strain AP37, *A. pleuropneumoniae* serotype 5 strain AP213 and *A. pleuropneumoniae* serotype 7 strain AP76, were isolated from the lungs of diseased pigs given to the Western College of Veterinary Medicine, University of Saskatchewan, Saskatoon, Saskatchewan, Canada. The other *A. pleuropneumoniae* strains were field isolates from herds in Saskatchewan. The *E. coli* strain HB101 (hsdM, hsdR, recA) was used in all transformations using plasmid DNA. *E. coli* strains NM538 (supF, hsdR) and NM539 (supF, hsdR, P2cox) served as hosts for the bacteriophage λ library. The plasmids pGH432 and pGH433 are expression vectors containing a tac promoter, a translational start site with restriction enzyme sites allowing ligation in all three reading frames followed by stop codons in all reading frames.

*A. pleuropneumoniae* strains were grown on PPLO medium (Difco Laboratories, Detroit, Mich.) supplemented with 1% IsoVitalex (BBL Microbiology Systems, Becton Dickinson & Co., Cockeysville, Md. 21030). Plate cultures were incubated in a $CO_2$-enriched (5%) atmosphere at 37° C. Liquid cultures were grown with continuous shaking at 37° C. without $CO_2$ enrichment.

Iron restriction was obtained by adding 2,2 dipyridyl to a final concentration of 100 μmol. Heat stress was induced by transferring cultures to 45° C. for 2 hours. Ethanol stress was exerted by the addition of 10% (vol/vol final concentration) of absolute ethanol to cultures in mid log phase. Oxidative stress was induced by the addition of 1% (vol/vol final concentration) of 30% $H_2O_2$ to the cultures. *E. coli* transformants were grown in Luria medium (Maniatis, T., et al., *Molecular Cloning: A Laboratory Manual* (1982) Cold Spring Harbor Laboratory, Cold Spring Harbor, N.Y.) supplemented with ampicillin (100 mg/l).

Preparation and Analysis of Culture Supemtants Outer Membranes and Protein Aggregates Culture supernatants were mixed with two volumes of absolute ethanol and kept at −20° C. for 1 h. Precipitates were recovered by centrifugation and resuspended in water. Outer membranes were prepared by sarkosyl solubilization as previously described (Deneer, H. G., and Potter, A. A., *Infect. Immun.* (1989) 57:798–804). For the preparation of protein aggregates, broth cultures (50 ml) in mid log phase ($OD_{660}$ of 0.6) were induced by the addition of 1 mmol isopropylthiogalactoside (IPTG; final concentration). After 2 hours of vigorous shaking at 37° C., cells were harvested by centrifugation, resuspended in 2 ml of 25% sucrose, 50 mmol Tris/HC1 buffer pH 8, and frozen at −70° C. Lysis was achieved by the addition of 5 μg of lysozyme in 250 mmol Tris/HCl buffer pH 8 (5 min on ice), addition of 10 ml detergent mix (5 parts 20 mmol Tris/HCl buffer pH 8 (5 min on ice), addition of 10 ml detergent mix (5 parts 20 mmol Tris/HCl buffer pH 7.4, 300 mmol NaCl, 2% deoxycholic acid, 2% NP-40, and 4 parts of 100 mmol Tris/HCl buffer pH 8, 50 mmol ethylenediamine tetraacetic acid, 2% Triton X-100), and by sonication. Protein aggregates were harvested by centrifugation for 30 min at 15,000 g. Aggregate protein was resuspended in $H_2O$ to a concentration of 5–10 mg/ml and solubilized by the addition of an equal volume of 7 molar guanidine hydrochloride.

Proteins were analyzed by discontinuous sodium dodecylsulfate polyacrylamide gel electrophoresis (SDS PAGE) according to the method of Laemmli (Laemmli, M. K., *Nature* (1970) 227:680–685). The protein concentration was determined using a modified Lowry protein assay which prevents reaggregation of the protein. Bovine serum albumin (Pierce Chemical Co., Rockford, Ill.) was used as a standard. Briefly, samples were taken up in 0.5 ml of 1% sodium dodecyl sulfate (SDS), 0.1 mol NaOH, and 1.5 ml of 0.2 mol $Na_2CO_3$, 0.07 mol $NaKC_4H_4O_6 \cdot 4H_2O$, 0.1 mol NaOH, 0.001 mol $CuSO_4 \cdot 5H_2O$ were added. After 15 min incubation at 20° C. 0 15 ml of phenol reagent, diluted 1:2 with distilled water, was added. Samples were incubated at 55° C. for 15 min, and the optical density at 660 nm was determined.

Electrophoretic transfer onto nitrocellulose membranes was performed essentially as described by Towbin et al. (Towbin et al., *Proc. Natl. Acad. Sci. U.S.A.* (1979) 76:4350–4354). Nonspecific binding was blocked by incubation in 0.5% gelatine in washing buffer (150 mmol saline, 30 mmol Tris-HCl, 0.05% Triton-X100). Antibody and alkaline phosphatase conjugate (Kirkegaard & Perry Laboratories, Inc., Gaithersburg, Md.) were added in washing buffer, and each incubated for 1 h at room temperature. Blots were developed with a substrate containing 5-bromo-4-chloro-3-indolyl phosphate (BCIP) and nitro blue tetrazolium (NBT); ImmunoSelect, BRL, Gaithersburg, Md.) in 100 mmol Tris/HCl buffer pH 9.5, 50 mmol NaCl, 5 mmol $MgCl_2$.

Preparation of Antisera

Convalescent serum was obtained as follows. Pigs were given $10^3$ *A. pleuropneumoniae* intranasally and were challenged 2 weeks later with 2 LD50. Serum against the recombinant protein was raised in mice by intraperitoneal injection of 30 µg of solubilized aggregate in complete Freund's adjuvant and a subcutaneous boost with 30 µg protein in incomplete Freund's adjuvant two weeks later.

Iron Compounds

Transferrins from different species were obtained commercially (porcine transferrin from The Binding Site, Birmingham, UK; human and bovine transferrin from Sigma Chemical Co.). Porcine transferrin was iron depleted as described by Mazurier and Spik (Mazurier, J., and G. Spik, *Biochim. Biophys. Acta* (1980) 629:399–408). The resulting porcine apotransferrin as well as the commercially obtained bovine and human apotransferrins were iron repleted as described by Herrington and Sparling (Herrington, D. A., and F. P. Sparling, *Infect. Immun.* (1985) 48:248–251).

Transferrin Binding Assays

To assess the possible transferrin binding ability of recombinant proteins, a Western blot-like transferrin binding assay was performed essentially as described by Morton and Williams (Morton, D. J., and P. Williams, *J. Gen. Microbiol.* (1990) 136:927–933). During the entire procedure the temperature was kept below 37° C. Blots were developed using biotinylated transferrin (Biotin-XX-NHS Ester Labeling Kit, Clontech Laboratories, Palo Alto, Calif.) coupled to streptavidin phosphatase and purified by gel filtration using a G-100 column. In order to determine species specificity of transferrin binding, a competitive ELISA was developed. ELISA plates (Immulon 2, Dynatech Laboratories, McLean, Va.) were coated with 100 µl of porcine transferrin at a concentration of 100 µg/ml in carbonate buffer at 4° C. over night. All subsequent steps were performed at room temperature. Plates were blocked with 0.5% gelatine in washing buffer. Solubilized protein at a concentration of approximately 5 µg/ml was incubated in washing buffer for 1 hour with an equal volume of serial two fold dilutions of porcine, bovine, and human transferrin. Subsequently, 200 µl of this solution were added to the coated and washed wells and incubated for one hour. The assay was developed using a mouse serum raised against the recombinant protein, an alkaline phosphatase labeled conjugate and p-nitrophenyl phosphate in 1 mol diethanolamine, pH 9.5, 5 mmol $MgCl_2$ as substrate. The plates were read at 405 nm in a Biorad plate reader, and 50% inhibition values were determined for the various transferrins.

EXAMPLES

Example 1

Fractionation of Hot Saline Extracts

Vaccination of pigs with cell free extracts reduces mortality following experimental challenge. However, the presence of an uncharacterized immunosuppressive component can interfere with the induction of protective immunity in a dose dependent fashion. Therefore, an attempt was made to remove this component by preparative isoelectrofocusing. Cell free extracts were prepared as follows. *Actinobacillus pleuropneumoniae* serotype 1 strain AP37 was grown to mid log phase in PPLO broth supplemented with Isovitalex and the bacteria harvested by pelleting cells by centrifugation at 8,000×g for 15 minutes. Cells were resuspended in ¹/₁₀ volume of 0.85% sodium chloride and the mixture was shaken with glass beads at 60° C. for 1 hour. Cells were removed by centrifugation as described above and the supernatant material filter sterilized. This material was dialyzed against distilled water to remove the sodium chloride, mixed with Biorad ampholytes (pH range 3–11) and loaded in a Rotafor isoelectrofocusing cell. The mixture was focused at 12 watts constant power for 4–6 hours. Fractions were pooled into four samples according to pH as shown below. This material was used to vaccinate groups of 6 pigs as shown below.

Group 1: Fraction A, pH=10.4
Group 2: Fraction B, pH=6.1
Group 3: Fraction C, pH=5.2
Group 4: Fraction D, pH=2.4
Group 5: Mixture, Fraction A–D
Group 6: Same as Group 5.
Group 7: Placebo (no antigen)

Figure 9:
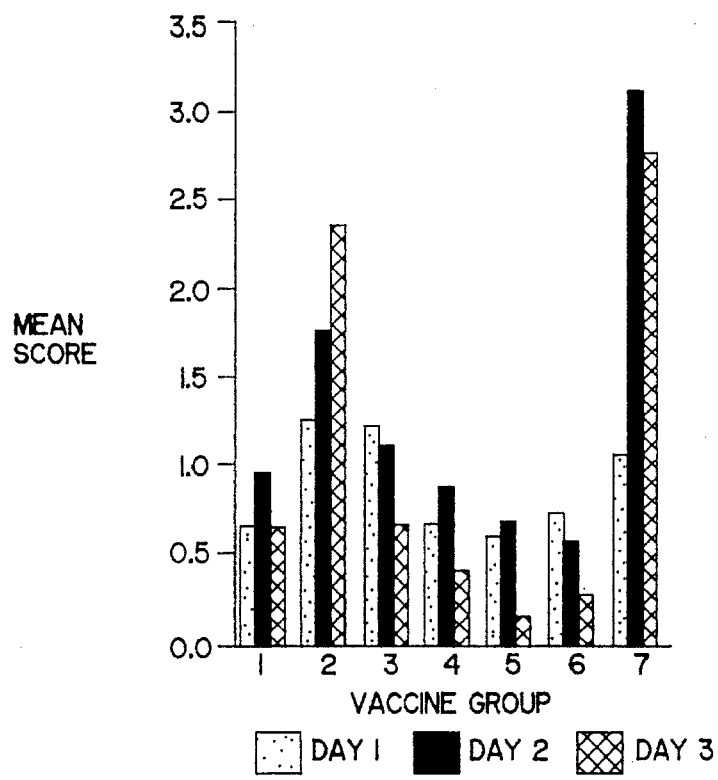
FIG. 9 shows the mean clinical scores of pigs given fractions from the hot saline extracts described in Example 1. Data for the first three days post challenge are shown. Clinical scores range from 0–4 with 4 indicating death.
Figure 10:
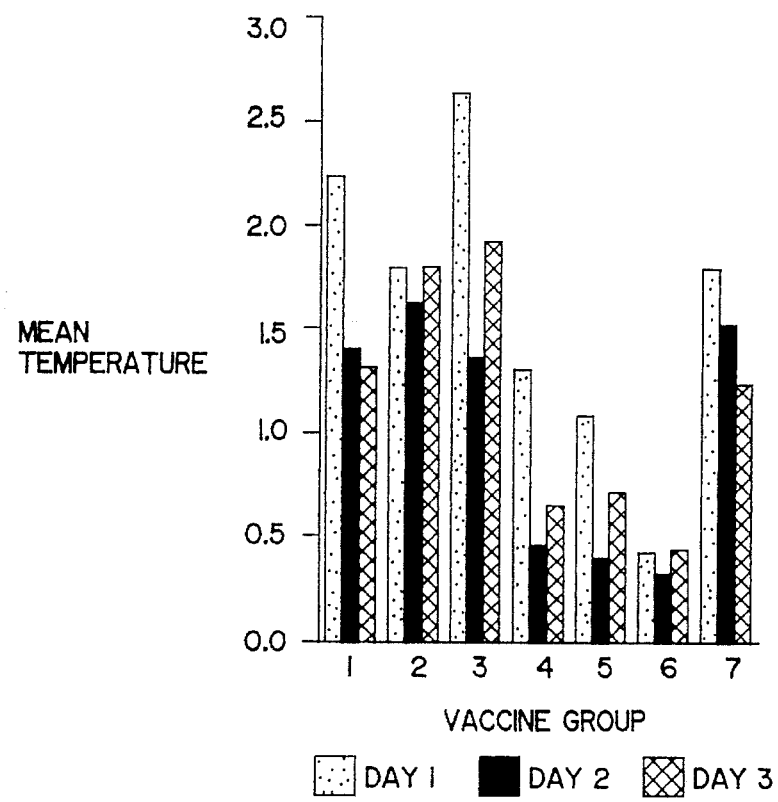
FIG. 10 depicts the mean body temperature of pigs given fractions from the hot saline extracts described in Example 1. Data for the first three days post challenge are shown. The values presented are degrees centigrade above 39° C.
Figure 11:
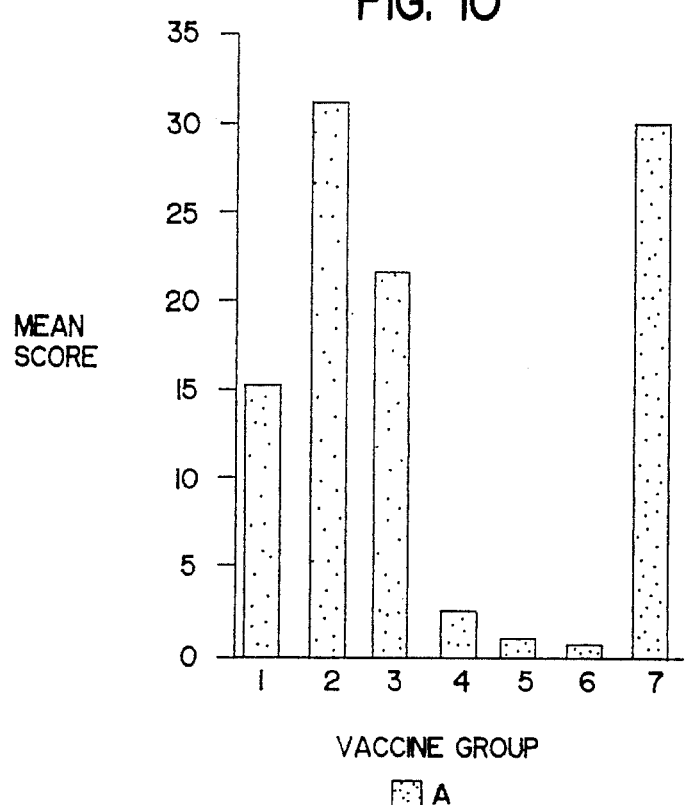
FIG. 11 depicts the mean lung scores of pigs given fractions from the hot saline extracts described in Example 1. Lungs were removed at necropsy and scored for the number and size of Porcine Haemophilus Pleuropneumonia lesions. Results are presented as percent of lung area.
Figure 12A:
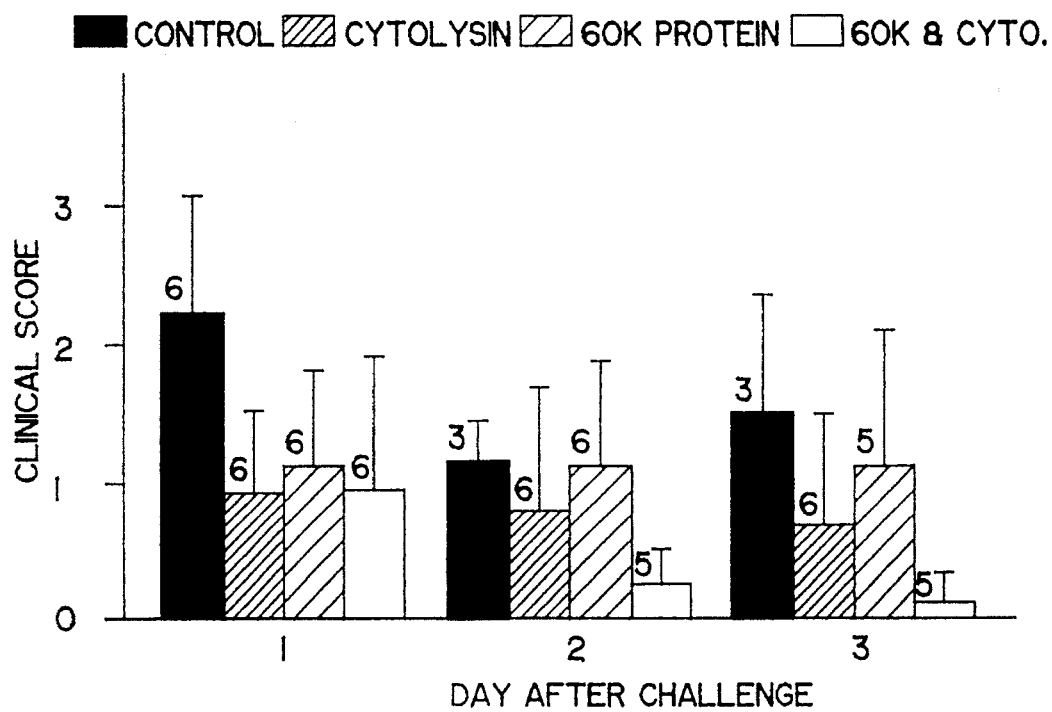
Figure 12B:
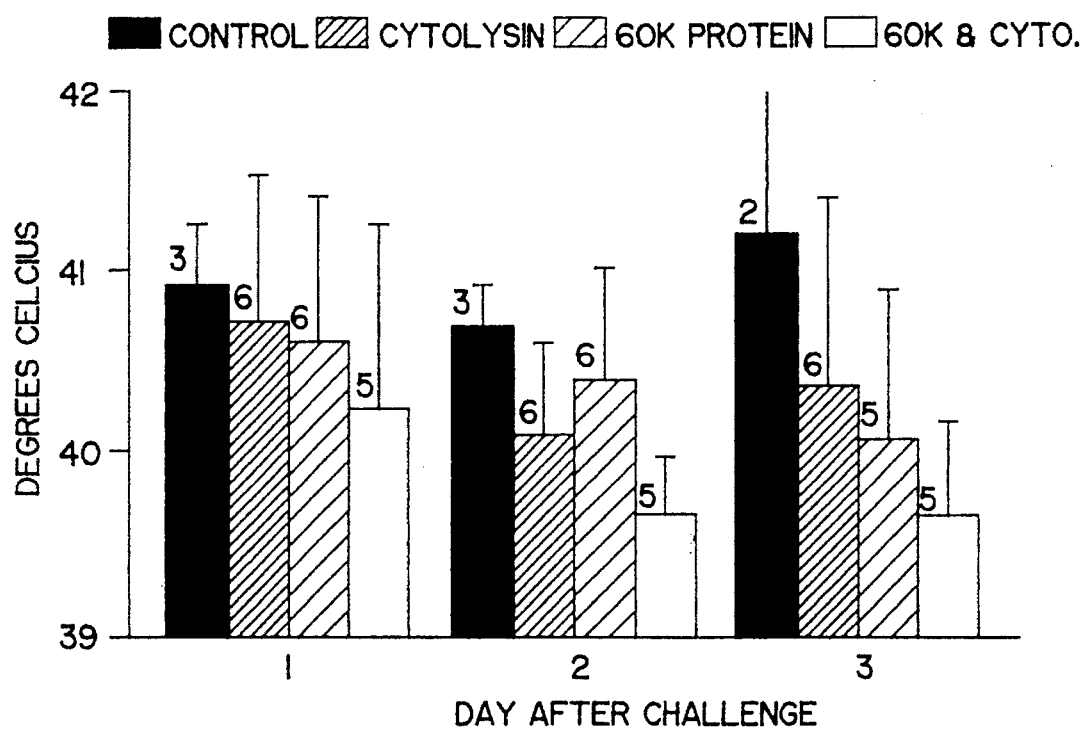
Figure 13A:
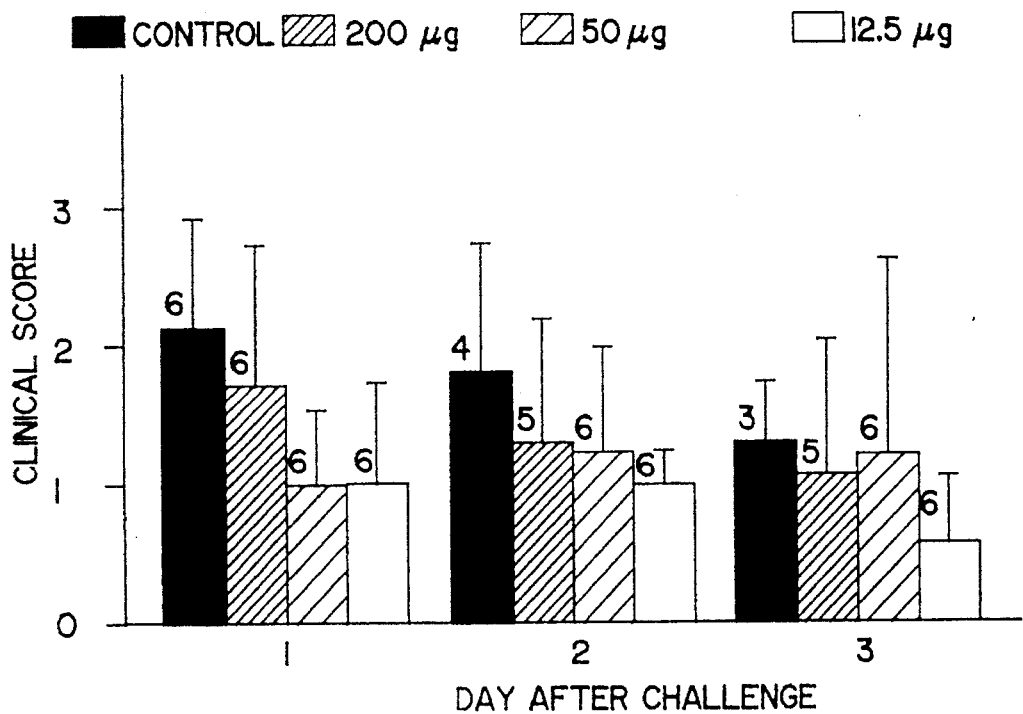
Figure 13B:
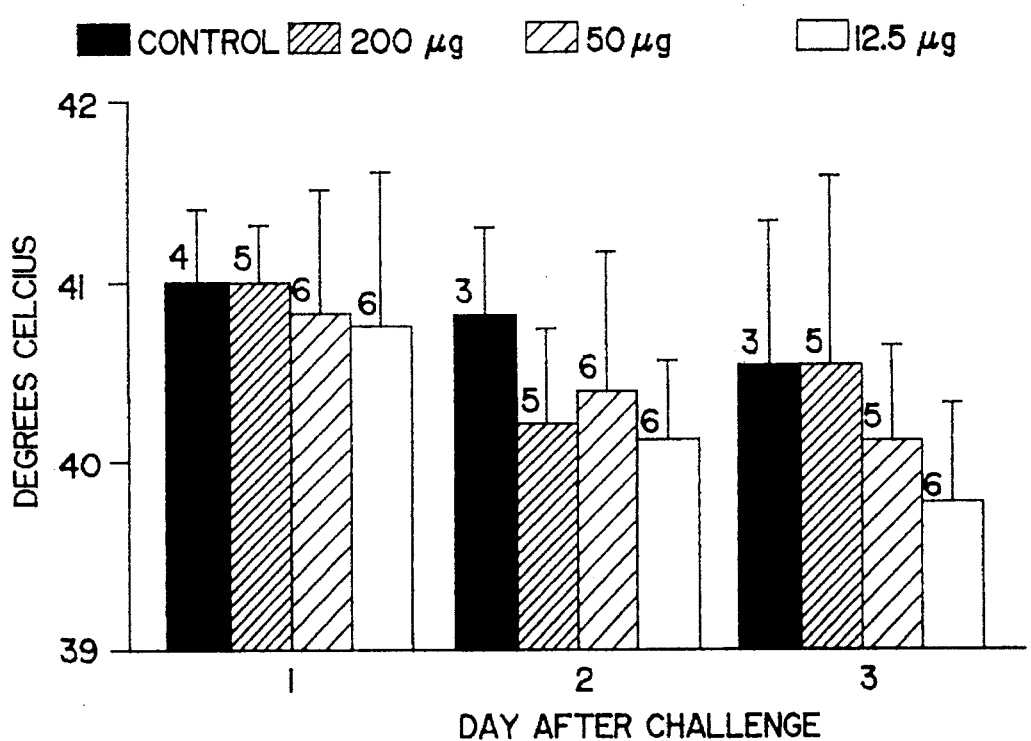

Marcol-52 was used as an adjuvant, and all pigs were boosted with the appropriate vaccine formulation after 3 weeks. After an additional week, all pigs were exposed to an aerosol of *Actinobacillus pleuropneumoniae* strain AP37 and clinical data plus body temperatures were recorded daily. In addition, serum samples collected at days 0, 21 and 34 of the trial were used to determine the serological response to vaccination by an enzyme linked immunosorbent assay (ELISA). The results are summarized in FIGS. 8 through 11. Pigs in Groups 1, 4, 5 and 6 all had significantly increased ELISA titers compared to the control group while those in Group 2 and 3 were only marginally better. These results were reflected in the mean clinical scores (FIG. 9), mean temperatures (FIG. 10) and mean lung scores (FIG. 11). Clearly, those pigs which received Fraction D or the mixture of all four Fractions were protected against experimental challenge. Furthermore, it appeared that these vaccine preparations reduced colonization of the lung, which can be a measure of chronicity.

Each of the above fractions was analyzed by polyacrylamide gel electrophoresis and Western blotting using sera collected from each pig prior to challenge. Fractions A and B contained little protein but a substantial quantity of lipopolysaccharide and lipoprotein. Fraction C contained a small quantity of protein, largely four components with molecular weights ranging from 100,000 to 14,000. Fraction D, which exhibited the greatest protective capacity, had the largest quantity of protein and contained at least 22 different components. However, only 7 proteins were present in significant amounts. Western blots revealed the presence of four strongly reactive proteins in Fractions C and D. These proteins had molecular weights of approximately 20 kDa, 40 kDa, 75 kDa and 100 kDa.

Example 2

Cloning of Genes Coding for

Serotype 1 Protective Proteins

All restriction enzyme digests were done in T4 DNA polymerase buffer (Maniatis, T., et al., *Molecular Cloning: A Laboratory Manual* (1982) Cold Spring Harbor Laboratory, Cold Spring Harbor, N.Y.) containing 1 mmol dithiothreitol and 3 mmol spermidine. *A. pleuropneumoniae* AP37 genomic DNA was prepared as previously described (Stauffer, G. V., et al., *Gene* (1981) 14:63–72) and partially digested with the restriction endonuclease Sau3AI. Fragments of 3000 to 8000 Bp were isolated by sucrose density gradient centrifugation (Maniatis, supra) and ligated into pGH432 and pGH433 which had been digested with BamHI and/or BglII. The ligated DNA was used to transform *E. coli* strain JM105. The colonies were transferred to nitrocellulose membranes, induced with IPTG and screened for reaction with serum from pigs vaccinated with Fraction D of the hot saline extract (above). Three positive clones which expressed Actinobacillus proteins were selected for further study. The restriction endonuclease maps of the three plasmids are shown in FIG. 6. One clone, prAPP4 (FIG. 6.1), codes for the serotype 1 APP4. Another clone (pTF37/E1, FIG. 6.2) codes for a putative serotype 1 transferrin binding protein, based on homology with its serotype 7 homolog (see below and FIG. 3; SEQ ID NOS:5 and 6). The nucleotide sequence of the gene coding for this protein was determined using the chain termination method as described by Sanger, F., et al., *Proc. Natl. Acad. Sci. USA* (1977) 7.4:5463–5467. Nested deletions were prepared by exonuclease III treatment, and specific primers were prepared using a Pharmacia Gene Assembler. Sequences were analyzed using the IBI/Pustell program and the Genbank network. The nucleotide sequence and deduced amino acid sequence are depicted in FIG. 2 SEQ ID NOS:3 and 4.

Example 3

Cloning of *Actinobacillus pleuropneumoniae*

Serotype 7 60 kDa Transferrin Binding Protein

As above, all restriction enzyme digests were done in T4 DNA polymerase buffer (Maniatis, supra) containing 1 mmol dithiothreitol and 3 mmol spermidine. Genomic DNA libraries of *A. pleuropneumoniae* serotype 7 strain AP205 were prepared as previously described (Stauffer, supra) and partially digested with the restriction endonuclease Sau3AI. Fragments of 1500 to 2500 Bp were isolated by sucrose density gradient centrifugation (Maniatis, supra) and ligated into pGH432 and pGH433. *E. coli* HB101 transformants were replica plated onto nitrocellulose membranes, induced for 2 hours on plates containing 1 mM IPTG and screened for reaction with serum from pigs infected with serotype 7 *A. pleuropneumoniae*. Positive transformants were replated, induced with IPTG and whole cell proteins were analyzed by Western blotting. A whole cell lysate of *A. pleuropneumoniae* grown under iron limiting conditions was used as a control.

Figure 7A:
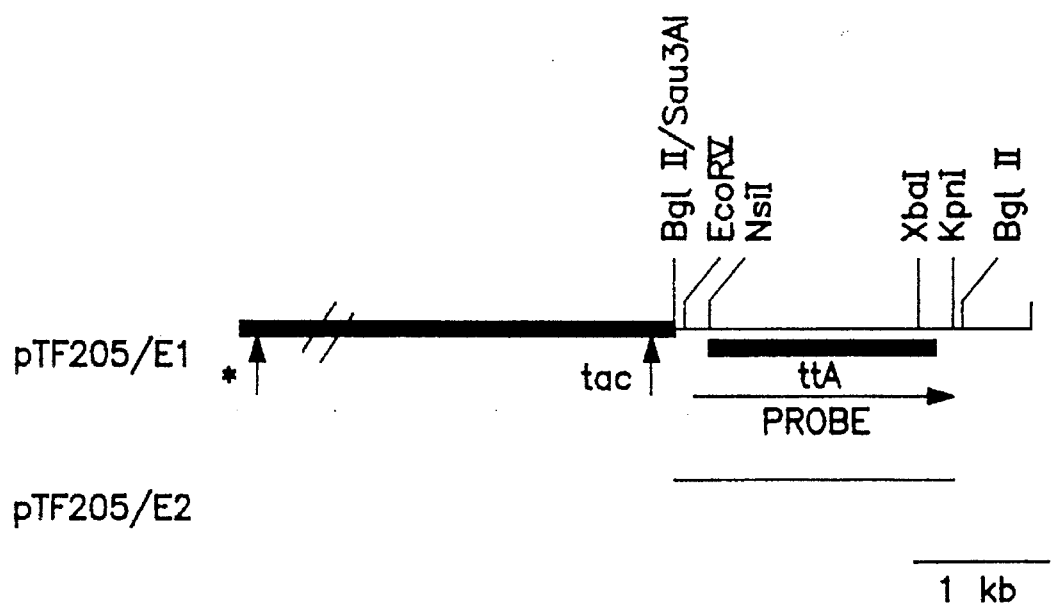
FIGS. 7A–7B show a physical map and the translational activity of plasmid pTF205/E1 and its deletion derivative, pTF205/E2. (A) The thick line represents DNA of the cloning vehicle (pGH433); tac indicates the location of the tac promoter, and the asterisk indicates stop codons in all three reading frames. The horizontal arrow indicates the location and direction of transcription of the encoded protein; as indicated, this DNA fragment was also used as a probe. (B) Depiction of an SDS gel of the IPTG induced aggregate proteins produced by pTF205/E1 (lane 1) and pTF205/E2 (lane 2); the molecular weight standards (lane 3) are phosphorylase b (97,400), bovine serum albumin (66.20), ovalbumin (45,000), and carbonic anhydrase (31,000).
Figure 7B:
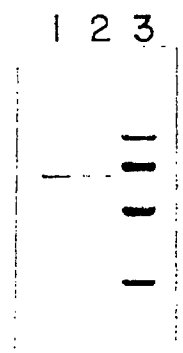
Figure 8:
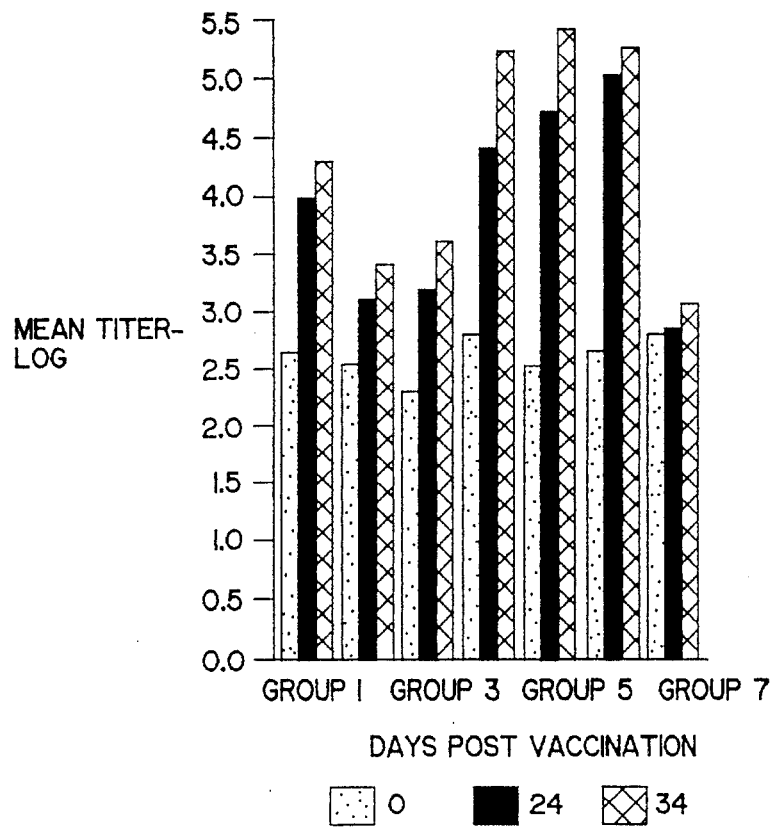
FIG. 8 shows the mean ELISA titers (log) from serum collected from pigs prior to vaccination with fractions from the hot saline extracts from Example 1, at day 24 and day 34 after vaccination. Mean values were calculated for each vaccine group. The background level of 2.5–3.0 is normal for Actinobacillus free pigs.

Of approximately 6000 transformants screened by immunoblotting, 22 reacted with convalescent serum and showed an immunoreactive band in the Western blot analysis. One transformant expressed a protein with the same electrophoretic mobility as an *A. pleuropneumoniae* polypeptide present only under iron limiting growth conditions. The plasmid present in this transformant was designated pTF205/E1 (FIG. 7A). The recombinant polypeptide produced by this strain had a molecular weight of 60,000 (FIG. 7B) and was produced as inclusion bodies, indicating that it was under the control of the tac promoter. Aggregated protein prepared from pTF205/E2 (a BamHI/BglII deletion derivative of the original plasmid) was used to immunize mice. The resulting serum reacted with a single polypeptide in the whole cell lysates and in culture supernatants from *A. pleuropneumoniae* serotype 7 strain AP205 grown under iron limiting conditions. Outer membranes prepared by sarkosyl solubilization (Deneer, H. G., and Potter, A. A., *Infect. Immun.* (1989) 57:798–804) of cells grown under iron limiting conditions did not react with the antiserum. Likewise, whole cell lysates, culture supernatants and outer membranes from cells grown in iron replete media did not react with the antibody.

The recombinant protein separated by non-reducing polyacrylamide gel electrophoresis was found to bind alkaline phosphatase-labeled porcine transferrin. This binding was shown to be species specific in a competitive ELISA, where the binding of the solubilized protein to iron replete porcine transferrin could be inhibited completely only by iron replete porcine transferrin. Porcine apotransferrin also inhibited binding, but a higher+concentration was necessary. Using human and bovine iron-deplete and -replete transferrins, 50% inhibition could not be obtained even with concentrations 40 times higher than the inhibitory dose for porcine transferrin. In addition, relatively high concentrations of both hemin and Congo Red could inhibit transferrin-binding of the 60 kDa protein, whereas porcine hemoglobin, EDDA, dipyridyl, and ferric titrate failed to do so (Table 1).

Congo Red and hemin binding by *E. coli* transformants expressing this protein at low levels was detected by supplementing the ampicillin containing Luria agar with 1–10 μmol IPTG and 0.003% Congo Red or 0.02% hemin.

TABLE 1

Competitive ELISA Showing the Differences in Affinity of the Recombinant 60 kDa Protein Toward Transferrins of Various Species

| Solid Phase Antigen | Competitive Substances[1] | 50% Inhibition Values[2] | |
|---|---|---|---|
| | | [µ/ml] | [µmol] |
| porcine transferrin (TF) | porcine | 25[3] | 0.3 |
| | porcine aTF | 150 | 1.8 |
| | human TF/aTF | >1000[4] | >12.5 |
| | bovine TF/aTF | >1000[4] | >12.5 |
| | porcine TF, NH$_2$-terminus | 20 | 0.5 |
| | bovine hemin | 4 | 6.0 |
| | Congo Red | 25 | 35.0 |

[1]Also tested and completely noninhibitory were porcine hemoglobin (14 µmol), EDDA (100 µmol, iron-saturated), Dipyridyl (100 µmol, iron-saturated), and ferric citrate (10 mmol).
[2]Inhibition values state the concentration of transferrin necessary in the preincubation step in order to obtain an inhibition of 50% in the reaction between recombinant protein and solid phase transferrin.
[3]The value varied between different experiments betweeen 12.5 and 100 µg/ml; however, the relative difference in inhibitory activity between the various substances was contant.
[4]This concentration had an inhibitory effect, but it was below 50%.

Chromosomal DNA was prepared from 27 different clinical isolates of A. pleuropneumoniae belonging to 6 different serotypes digested with the restriction endonucleases BglII and EcoRV, and separated on an agarose gel. This fragment was chosen because the functional activity of the deletion plasmid pTF205/E2 localized the position of the serotype 7 60 kDa gene upstream of the BglII site. A Southern blot analysis using the EcoRV/BglII fragment of pTF205/E1 as a probe detected a fragment identical in size in all of the above A. pleuropneumoniae serotype 2, 4 and 7 strains as well as in one serotype 3 strain. In contrast, none of the serotype 1 and 5 strains reacted with the probe. Neither did the E. coli HB101 and Pasteurella haemolytica controls.

The nucleotide sequence of the gene coding for the transferrin binding protein was determined by the chain termination method as described in Example 2 and is shown in FIG. 1 (SEQ ID NO:1).

Example 4

Cloning of A. pleuropneumonia Serotype 7 Cytolysin Gent

A recombinant plasmid containing the carboxyterminal 70% of the 103 kDa serotype 7 cytolysin gene (cytA) was constructed as follows. A gene library of A. pleuropneumoniae serotype 7 strain AP76 was constructed in the phage vector λ2001. Plaques were screened by hybridization using the Pasteurella haemolytica lktA gene as a probe (see Lo, R.Y.C., et al., Infect. Immun. (1987) 55:1987–1996 for a description of this gene). Positive plaques were purified and a 16 kb EcoRI fragment was subcloned into the plasmid vector pACYC184 (plasmid pCY76/5, FIG. 5). A 3.5 kb BglII fragment from pCY76/5 was further subcloned into the BglII site of the expression vector pGH432 lacI which provides a 5 amino acid leader peptide and an IPTG inducible promoter (pCY76/503, FIG. 5). Nucleotide sequence analysis of the fusion site revealed sequence identity with the cytolysin from A. pleuropneumoniae serotype 5 (FIG. 4; SEQ ID NO:7 Chang, Y. F., et ai., DNA (1989) 8:635–647). Further analysis of the A. pleuropneumoniae cytolysin type II genes by Southern blotting revealed that the B and D genes are not located immediately downstream from the cytA gene on the Actinobacillus chromosome. This is unusual, as the cytolysin C, A, B and D genes are clustered in the A. pleuropneumoniae cytolysin type I (Frey, J., and Nicolet, J., J. Clin. Microbiol. (1990) 28:232–236), P. haemolytica leukotoxin (Strathdee, C. A. and Lo, R.Y.C., Infect. Immun. (1989) 171:916–928), and the E. coli alpha hemolysin (Welch, R. A. and Pellet, S. A. J. Bacteriol. (1988) 170:1622–1630).

E. coli HB101 containing plasmid pCY76/503 expressed the recombinant cytolysin (CytA) as inclusion bodies upon induction with IPTG. The protein made up 30% of the total protein content in the pCY76/503 transformants. Isolated protein aggregates were estimated to be 75% pure. The resulting protein could be detected by A. pleuropneumoniae convalescent serum and by antibodies raised against the A. pleuropneumoniae type 1 cytolysin-containing culture supernatant. Restriction endonuclease maps of the cytolysin gene and sequence data are shown in FIGS. 5 and 4.

Example 5

Isolation and Characterization of Spontaneous Mutants of the cytA Gene

Spontaneous deletions of the cytA gene from the A. pleuropneumoniae chromosome occur at high frequency (approximately 1/10,000 colonies), as determined by reaction with monospecific antisera against the cytolysin. In order to isolate and characterize the spontaneous mutants, A. pleuropneumoniae strains AP76 and AP205 were subcultured twice from single colonies. Two independent serial dilutions were made for each strain, and from each approximately 10,000 colonies were plated. After replica-plating onto nitrocellulose, three independent cytolysin-negative colonies were detected by immunoblot and designated AP76Δ1, AP205Δ1, and AP205Δ2. Western blot analysis of whole cell lysates revealed that these colonies lacked the cytolysin whereas the Coomassie blue stained total protein profile appeared to be identical with the wildtype. Southern blot analysis of restricted DNA from AP76Δ1 and AP205Δ1 with λCY76/5-derived probes revealed that the BglII fragment was absent, although hybridization was observed after using the BglII fragment as a probe. Hybridization with the BglII-EcoRI fragments located on either end of λCY76/5 resulted in the appearance of strong bands in the cytolysin-negative mutants, and the hybridizing EcoRI fragment appeared to be approximately 7 kb smaller than that in the wildtype.

In order to characterize the cytA excision site, a genomic library was prepared from AP76Δ1 and probed with the EcoRI fragment derived from λCY76/5. Several clones were isolated, and initial characterization revealed that one clone had a BamHI-KpnI fragment identical in size to that of λCY76/5. This clone was designated as λCY76Δ1/1. Also, the nucleotide sequence of the BamHI-KpnI fragment of this clone was identical to the corresponding region of λCY76/5. Part of this sequence was present a second time on λCY76/5 starting 358 bp downstream from the end of cytA (FIGS. 14 and 15; SEQ ID NOS: 9, 10 and 11). Further analysis showed that cytA is flanked by two identical direct repeats each being 1201 bp in length, and that one repeat is completely conserved in λCY76/Δ1. The sequence flanking the direct repeats located on either site of the cytA gene in λCY76/5 is TTAATG---AATATT, and this sequence does not comprise part of an apparent longer reading frame (FIG.

16; SEQ ID NO: 8). An initial analysis of the repeat sequence revealed that its ends form complementary repeats with 4 mismatches over a length of 26 bp. They also contain one open reading frame going in the opposite direction than cytA. The open reading frame is 1038 nucleotides long and preceded by a Shine-Dalgarno consensus sequence.

Example 6

The Protective Capacity of Serotype 7

Recombinant Proteins

*E. coli* HB101 strains expressing the transferrin binding protein and the 103 kDa cytolysin were grown to mid log phase in 50 ml broth cultures and induced by the addition of 2 mM IPTG. After two hours of vigorous Shaking at 37° C., cells were harvested by centrifugation and resuspended in 2 ml 50 mM of Tris-HCl, pH 8, 25% sucrose, and frozen at −70° C. The cell suspension was thawed, 5 μg of lysozyme added and after 5 min on ice, 10 ml of detergent mix was added to lyse cells. The lysed cell suspension was sonicated to reduce viscosity and protein aggregates were harvested by centrifugation for 30 min at 15,000 g. The aggregated protein was resuspended in double distilled water to a concentration of 5–10 mg/ml and solubilized by the addition of an equal volume of 7 M guanidine hydrochloride. The solubilized protein was diluted in distilled water to 1 mg/ml and emulsified in Amphigen (Smith-Kline Beecham, Lincoln, Nebr.) with Tween80 (Sigma Chemical Co., St. Louis, Mo.) and Span (Sigma Chemical Co., St. Louis, Mo.) using a Polytron homogenizer (Kinematica GmbH, Littau, Switzerland). Each 2 ml dose of vaccine contained Amphigen (100 μl), Tween80 (28 μl), Span (12 μl), guanidine hydrochloride (20 mmol), and protein as indicated below.

Trial 1: 48 pigs were randomly assigned to 8 groups and immunized by intramuscular injection in the neck muscle twice (on days 1 and 21) as follows: 2 groups received 25 μg of recombinant CytA, 2 groups received 25 μg of recombinant *A. pleuropneumoniae* serotype 7 60 kDa protein, 2 groups received both proteins, and 2 groups (unimmunized controls) received the adjuvant only. One set of 4 groups was subsequently challenged on day 32 with *A. pleuropneumoniae* serotype strain AP37 ($4.1\times10^5$ CFU/ml), the other one with *A. pleuropneumoniae* serotype 7 strain AP205 ($1.4\times10^8$ CFU/ml).

Trial 2: 24 pigs were randomly assigned to 4 groups, and the groups twice received 0, 12.5, 50, or 200 μg recombinant *A. pleuropneumoniae* serotype 7 60 kDa protein. Subsequently, all groups were challenged with $7\times10^8$ CFU/ml of *A. pleuropneumoniae* serotype 7 strain AP205.

Clinical data plus body temperatures were recorded daily for 3 days post challenge and each animal received a daily average clinical score. The scoring system is.defined as follows: 0 - clinically normal; 1 - slight increase in respiratory rate and effort, slight depression; 2 - marked increase in respiratory rate and effort, marked depression; 3 - severe increase in respiratory rate and effort, severe depression, mouth breathing and/or cyanotic. Animals with a clinical score of 3 were euthanized.

In addition, serum samples collected at days 0, 21 and 28 of the trial were used to determine the serological response to vaccination by an enzyme linked immunosorbent assay (ELISA). All serum samples were titrated in the ELISA against the recombinant serotype 7 60 kDa transferrin binding protein, the recombinant cytolysin protein, as well as against an *A. pleuropneumoniae* serotype 7 and serotype 1 extract (Willson, P. J., et al., *Can. Vet. J.* (1988) 29:583–585). Briefly, plates were coated overnight at 4° C. with 100 μl of a solution containing either 1 μg/ml of recombinant protein or 10 μg/ml of extract protein in carbonate buffer. Plates were blocked for 1 h at room temperature with 0.5% gelatine in washing buffer (150 mmol saline, 30 mmol Tris-HC1, 0.05% Tween20). An internal standard consisted of a pool of equal volumes of swine antisera to *A. pleuropneumoniae* serotype 1 and serotype 7 that was diluted 1:100 in washing buffer. Serum dilutions and goat-anti-pig alkaline phosphatase conjugate (Kirkegaard & Perry Laboratories, Inc., Gaithersburg, Md.) were each left to incubate for 1 h at room temperature. Plates were developed at 37° C. with 100 μl p-nitrophenyl phosphate (3 g/l) in 1 mol diethanolamine, 50 mmol $MgCl_2$, pH 9.8. The development time was varied for the different coating antigens such that the control serum had a titer between 1:800 and 1:1600 (10 min for the cytolysin, 20 min for the *A. pleuropneumoniae* serotype 1 extract, 45 min for the 60 kDa protein, 90 min for the *A. pleuropneumoniae* 7 extract).

The trials were terminated on day 40, and all surviving pigs were euthanized. The injection sites were examined, and lungs were scored to determine the percentage of pulmonary area affected by lesions using a computerized digitizer. Lungs were cultured to determine the presence of *A. pleuropneumoniae* and to confirm its serotype.

The significance of the difference in mortality rates among the different groups was determined using a $G^2$ likelihood ratio test (Dixon, W. J., et al., *BMDP Statistical Software Manual,* University of California Press, 1988, pp. 229–273.

The results are summarized in Tables 2 and 3. As can be seen, all pigs in Trial 1 developed a strong antibody response to the recombinant antigen with which they had been immunized (Table 2). There was a significant difference ($p<0.03$) in mortality among the 8 groups. After challenge with *A. pleuropneumoniae* serotype 7 (strain AP205), the mortality in all immunized groups was lower than in the control group ($p<0.1$). Also, the damage to the lungs of immunized pigs may be less extensive than that seen in the control pigs (Table 2). This outcome was reflected by a generally milder course of disease shown by lower body temperature and clinical scores during the first 3 days after challenge (FIGS. 12A and 12B). Pigs that developed an antibody response against both recombinant antigens showed a particularly mild course of disease (FIGS. 12A and 12B), and damage to their lungs was minimal (Table 2).

All pigs in trial 2 developed a strong antibody response to the 60 kDa protein, and the titers were independent of the dose (Table 3). The immunized groups had a lower mortality than the control group ($p=0.14$), and the lesion score of the lungs from pigs in group H was also reduced for immunized pigs (Table 2). These results are supported by the clinical data obtained in the first 3 days .after challenge (FIGS. 13A and 13B). Both mortality and clinical data do not show an increased efficacy of the higher antigen dose.

In both trials, the injection sites were free of macroscopically detectable alterations. In all pigs, *A. pleuropneumoniae* was isolated from the lungs 1 week after challenge.

In agreement with previous findings, our results show a lack of protection against a heterologous serotype despite an appreciable serum titer in the animals (Table 2). This lack of cross-protection could be explained by two observations:

(1) The *A. pleuropneumoniae* serotype 1 challenge strain not only expressed the 103 kDa cytolysin but, in addition, expressed a serologically distinct 105 kDa cytolysin. This is in accordance with the results of Kamp, E. M., et al., Abstr. CRWAD (1990) 1990:270, who described the presence of these two cytolysins in an *A. pleuropneumoniae* serotype 1 strain. Therefore, the lack of protection against heterologous challenge could not only be caused by serotype-specific differences of the 103 kDa cytolysin, but it could also indicate that the activity of one cytolysin is sufficient to allow subsequent colonization by the pathogen.

(2) The *A. pleuropneumoniae* serotype 1 and 7 challenge strains express different 60 kDa proteins. Thus, Southern hybridization of chromosomal DNA from the *A. pleuropneumoniae* serotype 1 challenge strain with the tfbA probe did not result in binding under high stringency conditions, and serum raised against the 60 kDa protein did not react strongly with *A. pleuropneumoniae* serotype 1 grown under iron-restricted conditions. The observations concerning the genetic and antigenic differences of the 60 kDa proteins in *A. pleuropneumoniae* serotype 1 and 7 strains, as well as the presence of two different cytolysins in *A. pleuropneumoniae* serotype 1 strains, explain these results. Therefore, these findings suggest that a vaccine containing at least two serologically and functionally distinct *A. pleuropneumoniae* cytolysins, as well as serotype-specific 60 kDa proteins, might offer cross-protection against clinical symptoms.

TABLE 2

Mortality, Lung Damage, and Serological Response of Pigs Vaccinated With Recombinant Cytolysin and 60K-protein (Trail 1)

| Group | Antigen for Vaccination | Mortality[1] | % Lung Damage[2] | Serotiter[3] Cytolysin | Serotiter[3] 60K-protein | Body Temperature[4] | Clinical Score |
|---|---|---|---|---|---|---|---|
| *A. pleuropneumoniae* Challenge Strain: AP 205 (serotype 7) | | | | | | | |
| 1 | None | 4/6 | 17.5 ± 10.4 | <200 | <200 | 40.7 ± 0.2 | 1.75 |
| 2 | Cytolysin | 0/6 | 14.1 ± 15.5 | 2400 | <200 | 40.1 ± 0.5 | 0.625 |
| 3 | 60 kDa Protein | 1/6 | 26.5 ± 26.4 | <200 | 9600 | 40.4 ± 0.7 | 1.0 |
| 4 | Cytolysin and 60 kDa Protein | 1/6[5] | 3.7 ± 4.5 | 800 | 19.200 | 39.7 ± 0.3 | 0.25 |
| *A. pleuropneumoniae* Challenge Strain: AP 37 (serotype 1) | | | | | | | |
| 5 | None | 4/6 | — | <200 | <200 | 41.4 ± 0.3 | 2.0 |
| 6 | Cytolysin | 5/6 | — | 1600 | <200 | 41.8 ± 0.6 | 1.875 |
| 7 | 60 kDa Protein | 4/6 | — | <200 | 19.200 | 41.4 ± 0.2 | 1.5 |
| 8 | Cytolysin and 60 kDa Protein | 4/6 | — | 1600 | 6400 | 41.2 ± 0.6 | 1.75 |

[1]Number of pigs that died or were euthanized in extremis over the total in the group.
[2]The lung damage was assessed only for pigs surviving until day 7 after challenge.
[3]The serotiter is the median of the individual titers determined at the date of challenge.
[4]Arithmetic mean body temperature (c) for survivors on the second day after challenge.
[5]The dead pig did not develop a serotiter against the cytolysin.

TABLE 3

Mortality, Lung Damage, and Serological Response of Pigs Vaccinated With Different Amounts of Recombinant 60 kDa Protein (Trail 2)

| *A. pleuropneumoniae* Challenge Strain | Group | Amount [µg] of Antigen for Vaccination | Mortality[1] | % Lung Damage[1] | Serotiter[2] |
|---|---|---|---|---|---|
| AP205 (serotype 7) | 1 | None | 3/6 | 8.6 ± 6.1 | <200 |
| | 2 | 200 | 1/6 | 7.0 ± 4.9 | 51.200 |
| | 3 | 50 | 1/6 | 11.9 ± 15.0 | 25.600 |
| | 4 | 12.5 | 0/6 | 7.3 ± 10.2 | 51.200 |

[1]The lung damage was assessed only for pigs surviving until day 7 after challenge.
[2]The serotiter is the median of the individual titers determined at the date of challenge.

Example 7

Cloning of *A. Pleuropneumoniae* Serotype 5 Protective Proteins

A genomic library of *A. pleuropneumoniae* serotype-5 strain AP213 was prepared by partially digesting chromosomal DNA with Sau3AI and ligating into the BamHI site of the phage vector λ2001 as described in Example 4. The library was screened under low stringency conditions with an NsiI-KpnI fragment from plasmid pTF205/E1, which encodes the serotype 7 transferrin binding protein (tfbA), and with probes from the gene encoding the APP4 protein from serotype 1. The DNA from positive plaques of each type was purified and subcloned into expression vectors as follows. For the rAPP4 gene, recombinant λ2001 DNA was partially digested with Sau3AI and ligated into a BamHI-digested pGH432. The ligation mix was transformed into *E. coli* HB101. For the tfbA gene, an NsiI fragment from the recombinant phage was subcloned into the NsiI site of plasmid pTF205/E1, in front of the serotype 7 tfbA gene. This ligation mix was also transformed into *E. coli* HB101. This construct was trimmed by digesting the plasmid completely with BamHI and partially with Sau3AI and religating. This eliminated the *A. pleuropneumoniae* serotype 7 tfbA gene and non-coding DNA at the 3' end of serotype 5 tfbA the gene.

The recombinant plasmids expressing the serotype 5 tfb gene (pTF213/E6) and the rAPP4 gene (p#4-213-84) were shown to produce polypeptides of approximately 62 kDa and 60 kDa, respectively, which reacted with convalescent serum from an *A. pleuropneumoniae* serotype 5-infected pig. In addition, serum raised against the recombinant tfbA protein reacted specifically with a 62 kDa protein of *A. pleuropneumoniae* serotype 5.

Example 8

The Protective Capacity of Serotype 5

Recombinant Proteins

Serotype 5 recombinant transferrin binding protein and recombinant APP4 were prepared as described in Example 7. Vaccines containing these recombinant proteins were prepared by solubilizing the proteins with guanidine hydrochloride and combining the resultant solution with the adjuvant Emulsigen Plus such that each 2 ml dose contained 25 μg protein and 30% adjuvant, as described in Example 6.

Groups of four pigs were vaccinated as described in Example 6 with the recombinant vaccines and three pigs were immunized with a placebo containing adjuvant only. All animals were boosted three weeks later, and after seven days allpigs were challenged with *A. pleuropneumoniae* serotype 5 strain AP213 ($8\times10^5$ CFU/ml) by aerosol as described in Example 6. Clinical signs of disease were monitored daily for three days post challenge, and one week after challenge. All surviving pigs were euthanized and their lungs were examined for pneumonic lesions.

As shown in Table 4, vaccination with either antigen eliminated mortality associated with *A. pleuropneumoniae* infection and reduced clinical signs of disease.

TABLE 4

Mortality and Clinical Signs of Disease in Pigs Vaccinated with Recombinant Serotype 5 Transferrin binding Protein or APP4

| Grp | Antigen for Vaccination | Mortality[1] | Clinical Score Day 1 | Day 2 | Day 3 | % Lung Damage[2] |
|---|---|---|---|---|---|---|
| 1 | Placebo | 3/3 | 1.33 | 1.58 | 2.13 | ND |
| 2 | Tfb[3] | 0/4 | 0.87 | 0.75 | 0.38 | 8.13 |
| 3 | rAPP4 | 0/4 | 1.31 | 1.25 | 1.37 | 18.73 |

[1]Number of pigs that died or were euthanized in extremis over the total in the group.

TABLE 4-continued

Mortality and Clinical Signs of Disease in Pigs Vaccinated with Recombinant Serotype 5 Transferrin binding Protein or APP4

| Grp | Antigen for Vaccination | Mortality[1] | Clinical Score Day 1 | Day 2 | Day 3 | % Lung Damage[2] |
|---|---|---|---|---|---|---|

[2]The lung score was assessed only for pigs surviving until day 7 after challenge.
[3]Transferrin binding protein.

Example 9

The Protective Capacity of Serotype 1

APP4 Protein

Serotype 1 recombinant APP4 was prepared as described in Example 7. Vaccines containing the APP4 protein were prepared by solubilizing the protein with guanidine hydrochloride and combining the resultant solution with the adjuvant Amphigen such that each 2 ml dose contained 25 μg protein and 30% adjuvant, as described in Example 6.

Groups of four pigs were vaccinated as described in Example 6 with the recombinant vaccine and three pigs were immunized with a placebo containing adjuvant only. All animals were boosted three weeks later, and after seven days all pigs were challenged with *A. pleuropneumoniae* serotype 1 strain AP37 by aerosol as described in Example 6. Clinical signs of disease were monitored daily for three days post challenge, and one week after challenge. All surviving pigs were euthanized and their lungs were examined for pneumonic lesions.

As shown in Table 5, vaccination with APP4 reduced mortality associated with *A. pleuropneumoniae* infection and reduced clinical signs of disease.

TABLE 5

Mortality and Clinical Signs of Disease in Pigs Vaccinated with Recombinant Serotype 1 APP4

| Group | | Mortality[1] | Clinical Score Day 1 | Day 2 | Day 3 |
|---|---|---|---|---|---|
| 1 | Placebo | 3/5 | 2.20 | 1.00 | 0.75 |
| 2 | APP4 | 1/6 | 0.58 | 1.00 | 0.30 |

[1]Number of pigs that died or were euthanized in extremis over the total in the group.

Thus, subunit vaccines for use against *A. pleuropneumoniae* are disclosed, as are methods of making and using the same. Although preferred embodiments of the subject invention have been described in some detail, it is understood that obvious variations can be made without departing from the spirit and the scope of the invention as defined by the appended claims.

We claim:

1. An isolated nucleotide sequence coding for an immunogenic *Actinobacillus pleuropneumoniae* transfertin binding protein, wherein said nucleotide sequence is selected from the group consisting of: a nucleotide sequence coding for a serotype 7 transferrin binding protein having a molecular mass of approximately 60 kDa as determined by SDS PAGE, a homolog of said serotype 7 coding sequence which encodes a serotype 2 transferrin binding protein and which hybridizes to said serotype 7 coding sequence as determined using Southern blot analysis, a homolog of said serotype 7 coding sequence which encodes a serotype 3 transferrin binding protein and which hybridizes to said serotype 7 coding sequence as determined using Southern blot analysis, a homolog of said serotype 7 coding sequence which encodes a serotype 4 transferrin binding protein and which hybridizes to said serotype 7 coding sequence as determined using Southern blot analysis, a nucleotide sequence encoding a serotype 1 transferrin binding protein having a molecular mass of approximately 65 kDa as determined by SDS PAGE, and a nucleotide sequence encoding a serotype 5 transferrin binding protein having a molecular mass of approximately 62 kDa as determined by SDS PAGE.

2. The isolated nucleotide sequence of claim 1 wherein said transferrin binding protein comprises the amino acid sequence as depicted in FIGS. 1A–1E (SEQ ID NO:2).

3. The isolated nucleotide sequence of claim 1 wherein said transferrin binding protein comprises the amino acid sequence as depicted in FIGS. 2A–2D (SEQ ID NO:4).

4. The isolated nucleotide sequence of claim 1 which comprises the serotype 5 tfb gene nucleotide sequence present in recombinant plasmid pTF213/E6 (ATCC accession no. 69084).

5. A DNA construct comprising an expression cassette comprised of:

(a) a coding sequence as claimed in claim 1, and (b) control sequences that are operably linked to said coding sequence whereby said coding sequence can be transcribed and translated in a host cell, and at least one of said control sequences is heterologous to said coding sequence.

6. The DNA construct of claim 5 wherein said DNA coding sequence encodes an *Actinobacillus pleuropneumoniae* serotype 7 60 kDa transferrin binding protein.

7. The DNA construct of claim 5 wherein said DNA coding sequence encodes an *Actinobacillus pleuropneumoniae* serotype 5 62 kDa transferrin binding protein.

8. The DNA construct of claim 5 wherein said DNA coding sequence encodes an *Actinobacillus pleuropneumoniae* serotype 1 65 kDa transferrin binding protein.

9. A host cell stably transformed by a DNA construct according to claim 5.

10. A host cell stably transformed by a DNA construct according to claim 6.

11. A host cell stably transformed by a DNA construct according to claim 7.

12. A host cell stably transformed by a DNA construct according to claim 8.

13. A method of producing a recombinant polypeptide comprising:

(a) providing a population of host cells according to claim 9; and (b) growing said population of cells under conditions whereby the polypeptide encoded by said expression cassette is expressed.

14. A method of producing a recombinant polypeptide comprising:

(a) providing a population of host cells according to claim 10; and (b) growing said population of cells under conditions whereby the polypeptide encoded by said expression cassette is expressed.

15. A method of producing a recombinant polypeptide comprising:

(a) providing a population of host cells according to claim 11; and (b) growing said population of cells under conditions whereby the polypeptide encoded by said expression cassette is expressed.

16. A method of producing a recombinant polypeptide comprising:

(a) providing a population of host cells according to claim 12; and (b) growing said population of cells under conditions whereby the polypeptide encoded by said expression cassette is expressed.

* * * * *

UNITED STATES PATENT AND TRADEMARK OFFICE

CERTIFICATE OF CORRECTION

PATENT NO. : 5,521,072

DATED : May 28, 1996

INVENTOR(S) : POTTER et al.

It is certified that error appears in the above-identified patent and that said Letters Patent is hereby corrected as shown below:

```
    Col. 53, line 10, please replace "transfertin"
with --transferrin--.
```

Signed and Sealed this

Eighteenth Day of August, 1998

*Attest:*

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2696 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 333..1973

( x i ) SEQUENCE DESCRIPTION: SEQ ID NO:1:

```
ACAATGCCAA  TATTAACCCA  ATCTATTCCA  CTTGAATTAC  CAACCTCCAG  TATTGAGAAA         60

AAAGATGAGC  CAAAAGATAT  CTTCAGAGTG  GCGATTAATC  CTACGGGCAT  TTATTTAGGC        120

GAGAAGCTAG  TGAATGAAGA  AGAATTAAAA  CAATCTTTTC  TGACAAAATT  TCAGGAAAAT        180

AAAAATACCG  TTATTGCTAT  TTCTGCGGAT  ATTTCCGTGG  AATATCAACA  TATCGTGAAA        240

GTCCTTGAAT  TAGCTCAAAA  CGTCGGGCTA  ACGAAAATAG  GCTTTGTGAC  TCACCTAGTA        300

AATAAAAGCA  GAAATTTTAT  ATTGGAGGCA  AT  ATG  CAT  TTT  AAA  CTT  AAT  CCC     353
                                        Met  His  Phe  Lys  Leu  Asn  Pro
                                         1                 5

TAT  GCG  TTA  GCG  TTT  ACT  TCG  CTG  TTT  CTT  GTC  GCT  TGT  TCT  GGC  GGA   401
Tyr  Ala  Leu  Ala  Phe  Thr  Ser  Leu  Phe  Leu  Val  Ala  Cys  Ser  Gly  Gly
          10                      15                      20

AAA  GGA  AGT  TTT  GAT  TTA  GAA  GAT  GTC  CGG  CCT  AAT  AAG  ACA  ACA  GGC   449
Lys  Gly  Ser  Phe  Asp  Leu  Glu  Asp  Val  Arg  Pro  Asn  Lys  Thr  Thr  Gly
     25                      30                      35

GTG  TCT  AAA  GAG  GAG  TAC  AAG  GAT  GTA  GAA  ACA  GCC  AAG  AAA  GAA  AAA   497
Val  Ser  Lys  Glu  Glu  Tyr  Lys  Asp  Val  Glu  Thr  Ala  Lys  Lys  Glu  Lys
40                      45                      50                      55

GAA  CAG  TTA  GGG  GAA  TTA  ATG  GAA  CCT  GCT  TTG  GGG  TAT  GTT  GTA  AAA   545
Glu  Gln  Leu  Gly  Glu  Leu  Met  Glu  Pro  Ala  Leu  Gly  Tyr  Val  Val  Lys
                    60                      65                      70

GTT  CCG  GTG  AGT  TCT  TTT  GAA  AAT  AAG  AAA  GTT  GAT  ATT  TCA  GAT  ATA   593
Val  Pro  Val  Ser  Ser  Phe  Glu  Asn  Lys  Lys  Val  Asp  Ile  Ser  Asp  Ile
               75                      80                      85

GAA  GTG  ATT  ACG  AAC  GGA  AAT  TTA  GAC  GAT  GTG  CCG  TAC  AAG  GCA  AAT   641
Glu  Val  Ile  Thr  Asn  Gly  Asn  Leu  Asp  Asp  Val  Pro  Tyr  Lys  Ala  Asn
          90                      95                      100

TCA  TCT  AAA  TAT  AAC  TAT  CCA  GAT  ATA  AAA  ACA  AAA  GAT  TCT  TCT  CTT   689
Ser  Ser  Lys  Tyr  Asn  Tyr  Pro  Asp  Ile  Lys  Thr  Lys  Asp  Ser  Ser  Leu
     105                     110                     115

CAG  TAC  GTT  CGC  TCA  GGA  TAT  GTT  ATT  GAT  GGG  GAA  CAC  TCT  GGT  TCT   737
Gln  Tyr  Val  Arg  Ser  Gly  Tyr  Val  Ile  Asp  Gly  Glu  His  Ser  Gly  Ser
120                     125                     130                     135

AAT  GAA  AAG  GGA  TAT  GTG  TAT  TAT  AAA  GGT  AAT  TCA  CCT  GCA  AAA  GAA   785
Asn  Glu  Lys  Gly  Tyr  Val  Tyr  Tyr  Lys  Gly  Asn  Ser  Pro  Ala  Lys  Glu
                    140                     145                     150

TTA  CCC  GTT  AAT  CAG  CTT  TTA  ACT  TAT  ACA  GGA  AGT  TGG  GAT  TTT  ACT   833
Leu  Pro  Val  Asn  Gln  Leu  Leu  Thr  Tyr  Thr  Gly  Ser  Trp  Asp  Phe  Thr
               155                     160                     165

TCC  AAT  GCG  AAT  TTA  AAT  AAT  GAA  GAG  GGA  AGA  CCT  AAT  TAT  TTA  AAC   881
Ser  Asn  Ala  Asn  Leu  Asn  Asn  Glu  Glu  Gly  Arg  Pro  Asn  Tyr  Leu  Asn
          170                     175                     180

GAC  GAT  TAT  TAT  ACT  AAA  TTT  ATA  GGT  AAA  CGG  GTG  GGC  TTG  GTT  TCG   929
Asp  Asp  Tyr  Tyr  Thr  Lys  Phe  Ile  Gly  Lys  Arg  Val  Gly  Leu  Val  Ser
     185                     190                     195

GGA  GAT  GCG  AAA  CCT  GCA  AAG  CAT  AAA  TAC  ACT  AGC  CAG  TTT  GAA  GTT   977
Gly  Asp  Ala  Lys  Pro  Ala  Lys  His  Lys  Tyr  Thr  Ser  Gln  Phe  Glu  Val
200                     205                     210                     215
```

| | | | | | | | | | | | | | | | | |
|---|---|---|---|---|---|---|---|---|---|---|---|---|---|---|---|---|
| GAT | TTT | GCA | ACT | AAA | AAA | ATG | ACA | GGT | AAA | TTA | TCC | GAT | AAA | GAG | AAA | 1025 |
| Asp | Phe | Ala | Thr | Lys | Lys | Met | Thr | Gly | Lys | Leu | Ser | Asp | Lys | Glu | Lys | |
| | | | | 220 | | | | 225 | | | | | 230 | | | |
| ACG | ATT | TAT | ACA | GTC | AAT | GCT | GAT | ATT | AGA | GGC | AAT | CGT | TTT | ACG | GGG | 1073 |
| Thr | Ile | Tyr | Thr | Val | Asn | Ala | Asp | Ile | Arg | Gly | Asn | Arg | Phe | Thr | Gly | |
| | | | 235 | | | | | 240 | | | | | 245 | | | |
| GCT | GCT | ACA | GCG | AGT | GAT | AAA | AAT | AAA | GGG | AAA | GGC | GAA | TCA | TAT | AAC | 1121 |
| Ala | Ala | Thr | Ala | Ser | Asp | Lys | Asn | Lys | Gly | Lys | Gly | Glu | Ser | Tyr | Asn | |
| | | | 250 | | | | | 255 | | | | | 260 | | | |
| TTC | TTT | AGT | GCC | GAT | TCT | CAG | TCT | TTA | GAA | GGC | GGC | TTC | TAT | GGT | CCA | 1169 |
| Phe | Phe | Ser | Ala | Asp | Ser | Gln | Ser | Leu | Glu | Gly | Gly | Phe | Tyr | Gly | Pro | |
| | 265 | | | | | 270 | | | | | 275 | | | | | |
| AAA | GCA | GAA | GAA | ATG | GCA | GGG | AAA | TTT | GTA | GCT | AAC | GAC | AAA | TCT | CTT | 1217 |
| Lys | Ala | Glu | Glu | Met | Ala | Gly | Lys | Phe | Val | Ala | Asn | Asp | Lys | Ser | Leu | |
| 280 | | | | | 285 | | | | | 290 | | | | | 295 | |
| TTT | GCC | GTT | TTT | TCA | GCA | AAA | CAC | AAT | GGC | TCT | AAT | GTT | AAC | ACC | GTT | 1265 |
| Phe | Ala | Val | Phe | Ser | Ala | Lys | His | Asn | Gly | Ser | Asn | Val | Asn | Thr | Val | |
| | | | | 300 | | | | | 305 | | | | | 310 | | |
| CGG | ATT | ATT | GAT | GCC | TCA | AAA | ATT | GAT | TTA | ACT | AAT | TTC | AGC | ATT | TCA | 1313 |
| Arg | Ile | Ile | Asp | Ala | Ser | Lys | Ile | Asp | Leu | Thr | Asn | Phe | Ser | Ile | Ser | |
| | | | 315 | | | | | 320 | | | | | 325 | | | |
| GAA | CTT | AAC | AAT | TTT | GGT | GAT | GCT | TCC | GTT | TTA | ATT | ATT | GAT | GGG | AAA | 1361 |
| Glu | Leu | Asn | Asn | Phe | Gly | Asp | Ala | Ser | Val | Leu | Ile | Ile | Asp | Gly | Lys | |
| | | 330 | | | | | 335 | | | | | 340 | | | | |
| AAA | ATA | AAG | CTA | GCT | GGT | AGC | GGG | TTT | ACA | AAT | AAG | CAC | ACT | ATT | GAA | 1409 |
| Lys | Ile | Lys | Leu | Ala | Gly | Ser | Gly | Phe | Thr | Asn | Lys | His | Thr | Ile | Glu | |
| | 345 | | | | | 350 | | | | | 355 | | | | | |
| ATC | AAT | GGC | AAA | ACA | ATG | GTA | GCC | GTA | GCC | TGC | TGT | AGT | AAT | CTG | GAA | 1457 |
| Ile | Asn | Gly | Lys | Thr | Met | Val | Ala | Val | Ala | Cys | Cys | Ser | Asn | Leu | Glu | |
| 360 | | | | | 365 | | | | | 370 | | | | | 375 | |
| TAT | ATG | AAG | TTT | GGT | CAA | TTA | TGG | CAA | CAA | GCA | GAG | GGC | GGA | AAA | CCC | 1505 |
| Tyr | Met | Lys | Phe | Gly | Gln | Leu | Trp | Gln | Gln | Ala | Glu | Gly | Gly | Lys | Pro | |
| | | | | 380 | | | | | 385 | | | | | 390 | | |
| GAG | AAT | AAT | AGT | TTA | TTC | CTA | CAA | GGC | GAA | CGT | ACC | GCA | ACA | GAT | AAG | 1553 |
| Glu | Asn | Asn | Ser | Leu | Phe | Leu | Gln | Gly | Glu | Arg | Thr | Ala | Thr | Asp | Lys | |
| | | | 395 | | | | | 400 | | | | | 405 | | | |
| ATG | CCA | AAA | GGC | GGA | AAC | TAT | AAA | TAT | ATT | GGT | ACT | TGG | GAT | GCT | CAG | 1601 |
| Met | Pro | Lys | Gly | Gly | Asn | Tyr | Lys | Tyr | Ile | Gly | Thr | Trp | Asp | Ala | Gln | |
| | | 410 | | | | | 415 | | | | | 420 | | | | |
| GTT | TCA | AAA | GAA | AAT | AAC | TGG | GTT | GCT | ACG | GCA | GAT | GAT | GAT | AGA | AAA | 1649 |
| Val | Ser | Lys | Glu | Asn | Asn | Trp | Val | Ala | Thr | Ala | Asp | Asp | Asp | Arg | Lys | |
| | 425 | | | | | 430 | | | | | 435 | | | | | |
| GCT | GGC | TAT | CGG | ACA | GAA | TTT | GAT | GTT | GAT | TTT | GGC | AAC | AAA | AAT | TTA | 1697 |
| Ala | Gly | Tyr | Arg | Thr | Glu | Phe | Asp | Val | Asp | Phe | Gly | Asn | Lys | Asn | Leu | |
| 440 | | | | | 445 | | | | | 450 | | | | | 455 | |
| AGT | GGT | AAG | TTA | TTT | GAT | AAA | AAC | GGT | GTA | AAT | CCT | GTG | TTT | ACC | GTA | 1745 |
| Ser | Gly | Lys | Leu | Phe | Asp | Lys | Asn | Gly | Val | Asn | Pro | Val | Phe | Thr | Val | |
| | | | | 460 | | | | | 465 | | | | | 470 | | |
| GAT | GCA | AAA | ATT | GAT | GGT | AAT | GGT | TTT | ACT | GGC | AAA | GCT | AAA | ACC | TCA | 1793 |
| Asp | Ala | Lys | Ile | Asp | Gly | Asn | Gly | Phe | Thr | Gly | Lys | Ala | Lys | Thr | Ser | |
| | | | 475 | | | | | 480 | | | | | 485 | | | |
| GAT | GAA | GGC | TTC | GCT | CTA | GAT | TCA | GGT | AGT | TCA | CGT | TAT | GAG | AAT | GTG | 1841 |
| Asp | Glu | Gly | Phe | Ala | Leu | Asp | Ser | Gly | Ser | Ser | Arg | Tyr | Glu | Asn | Val | |
| | | 490 | | | | | 495 | | | | | 500 | | | | |
| AAA | TTT | AAC | GAT | GTA | GCA | GTT | AGT | GGT | GGC | TTC | TAT | GGT | CCA | ACG | GCA | 1889 |
| Lys | Phe | Asn | Asp | Val | Ala | Val | Ser | Gly | Gly | Phe | Tyr | Gly | Pro | Thr | Ala | |
| | 505 | | | | | 510 | | | | | 515 | | | | | |
| GCA | GAG | CTT | GGC | GGA | CAA | TTC | CAC | CAT | AAA | TCA | GAA | AAT | GGC | AGT | GTA | 1937 |
| Ala | Glu | Leu | Gly | Gly | Gln | Phe | His | His | Lys | Ser | Glu | Asn | Gly | Ser | Val | |
| 520 | | | | | 525 | | | | | 530 | | | | | 535 | |

```
GGT GCT GTC TTT GGT GCA AAA CAA CAA GTA AAA AAA TAATAAGGAA              1983
Gly Ala Val Phe Gly Ala Lys Gln Gln Val Lys Lys
            540                 545

TTTGCAATGA AAAATAAATT AAATCTGATT AGCCTTGCTC TGCTTAGCCT CTTTGCCGTA       2043

CAAAGCTATG CAGAACAAGC GGTGCAATTG AACGATGTTT ATGTCACAGG TACCAAAAAG       2103

AAAGCACATA AAAAGAGAA CGAAGTGACA GGCTTAGGGA AAGTAGTGAA AACACCAGAT        2163

TCTCTTAGTA AGGAGCAAGT GTTAGGAATG CGAGATCTGA CTCGCTACGA TCCGGGTATT       2223

TCTGTAGTAG AGCAAGGACG AGGTGCAACG ACAGGCTACT CAATTCGTGG GGTAGATCGT       2283

AATCGTGTGG GCTTGGCATT AGACGGTTTG CCACAGATTC AATCCTATGT AAGTCAATAT       2343

TCACGTTCCT CAAGCGGTGC CATTAATGAA ATAGAATACG AAAATCTGCG TTCGATCCAA       2403

ATTAGTAAAG GAGCTAGTTC TTCTGAGTTT GGCAGTGGCT CGCTAGGCGG TTCGGTGCAA       2463

TTCCGTACCA AAGAGGTAAG CGACATTATT AAGCCAGGGC AATCTTGGGG ACTAGATACC       2523

AAAAGTGCCT ACAGCAGCAA AAATCAACAA TGGTTAAACT CACTTGCTTT TGCGGGTACT       2583

CACAATGGCT TTGAGTCTCT TGTGATTTAC ACTCACCGTG ATGGTAAGGA AACGAAAGCT       2643

CATAAGGATG CAGAAAGCCG TTCTAAGAGT ATTCAGAGAG TGGATCTAAG CTT             2696
```

( 2 ) INFORMATION FOR SEQ ID NO:2:

( i ) SEQUENCE CHARACTERISTICS:
        ( A ) LENGTH: 547 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met His Phe Lys Leu Asn Pro Tyr Ala Leu Ala Phe Thr Ser Leu Phe
 1           5                  10                  15

Leu Val Ala Cys Ser Gly Gly Lys Gly Ser Phe Asp Leu Glu Asp Val
            20                  25                  30

Arg Pro Asn Lys Thr Thr Gly Val Ser Lys Glu Glu Tyr Lys Asp Val
            35                  40                  45

Glu Thr Ala Lys Lys Glu Lys Glu Gln Leu Gly Glu Leu Met Glu Pro
        50                  55                  60

Ala Leu Gly Tyr Val Val Lys Val Pro Val Ser Ser Phe Glu Asn Lys
65                  70                  75                  80

Lys Val Asp Ile Ser Asp Ile Glu Val Ile Thr Asn Gly Asn Leu Asp
                85                  90                  95

Asp Val Pro Tyr Lys Ala Asn Ser Ser Lys Tyr Asn Tyr Pro Asp Ile
            100                 105                 110

Lys Thr Lys Asp Ser Ser Leu Gln Tyr Val Arg Ser Gly Tyr Val Ile
            115                 120                 125

Asp Gly Glu His Ser Gly Ser Asn Glu Lys Gly Tyr Val Tyr Tyr Lys
        130                 135                 140

Gly Asn Ser Pro Ala Lys Glu Leu Pro Val Asn Gln Leu Leu Thr Tyr
145                 150                 155                 160

Thr Gly Ser Trp Asp Phe Thr Ser Asn Ala Asn Leu Asn Asn Glu Glu
                165                 170                 175

Gly Arg Pro Asn Tyr Leu Asn Asp Asp Tyr Tyr Thr Lys Phe Ile Gly
            180                 185                 190

Lys Arg Val Gly Leu Val Ser Gly Asp Ala Lys Pro Ala Lys His Lys
            195                 200                 205
```

| | | | | | | | | | | | | | |
|---|---|---|---|---|---|---|---|---|---|---|---|---|---|
| Tyr | Thr | Ser | Gln | Phe | Glu | Val | Asp | Phe | Ala | Thr | Lys | Lys | Met | Thr | Gly |
| | 210 | | | | 215 | | | | | 220 | | | | | |
| Lys | Leu | Ser | Asp | Lys | Glu | Lys | Thr | Ile | Tyr | Thr | Val | Asn | Ala | Asp | Ile |
| 225 | | | | | 230 | | | | | 235 | | | | | 240 |
| Arg | Gly | Asn | Arg | Phe | Thr | Gly | Ala | Ala | Thr | Ala | Ser | Asp | Lys | Asn | Lys |
| | | | | 245 | | | | | 250 | | | | | 255 | |
| Gly | Lys | Gly | Glu | Ser | Tyr | Asn | Phe | Phe | Ser | Ala | Asp | Ser | Gln | Ser | Leu |
| | | | 260 | | | | | 265 | | | | | 270 | | |
| Glu | Gly | Gly | Phe | Tyr | Gly | Pro | Lys | Ala | Glu | Glu | Met | Ala | Gly | Lys | Phe |
| | | 275 | | | | | 280 | | | | | 285 | | | |
| Val | Ala | Asn | Asp | Lys | Ser | Leu | Phe | Ala | Val | Phe | Ser | Ala | Lys | His | Asn |
| | 290 | | | | | 295 | | | | | 300 | | | | |
| Gly | Ser | Asn | Val | Asn | Thr | Val | Arg | Ile | Ile | Asp | Ala | Ser | Lys | Ile | Asp |
| 305 | | | | | 310 | | | | | 315 | | | | | 320 |
| Leu | Thr | Asn | Phe | Ser | Ile | Ser | Glu | Leu | Asn | Asn | Phe | Gly | Asp | Ala | Ser |
| | | | | 325 | | | | | 330 | | | | | 335 | |
| Val | Leu | Ile | Ile | Asp | Gly | Lys | Lys | Ile | Lys | Leu | Ala | Gly | Ser | Gly | Phe |
| | | | 340 | | | | | 345 | | | | | 350 | | |
| Thr | Asn | Lys | His | Thr | Ile | Glu | Ile | Asn | Gly | Lys | Thr | Met | Val | Ala | Val |
| | | 355 | | | | | 360 | | | | | 365 | | | |
| Ala | Cys | Cys | Ser | Asn | Leu | Glu | Tyr | Met | Lys | Phe | Gly | Gln | Leu | Trp | Gln |
| | 370 | | | | | 375 | | | | | 380 | | | | |
| Gln | Ala | Glu | Gly | Gly | Lys | Pro | Glu | Asn | Asn | Ser | Leu | Phe | Leu | Gln | Gly |
| 385 | | | | | 390 | | | | | 395 | | | | | 400 |
| Glu | Arg | Thr | Ala | Thr | Asp | Lys | Met | Pro | Lys | Gly | Gly | Asn | Tyr | Lys | Tyr |
| | | | | 405 | | | | | 410 | | | | | 415 | |
| Ile | Gly | Thr | Trp | Asp | Ala | Gln | Val | Ser | Lys | Glu | Asn | Asn | Trp | Val | Ala |
| | | | 420 | | | | | 425 | | | | | 430 | | |
| Thr | Ala | Asp | Asp | Arg | Lys | Ala | Gly | Tyr | Arg | Thr | Glu | Phe | Asp | Val |
| | | 435 | | | | | 440 | | | | | 445 | | | |
| Asp | Phe | Gly | Asn | Lys | Asn | Leu | Ser | Gly | Lys | Leu | Phe | Asp | Lys | Asn | Gly |
| | 450 | | | | | 455 | | | | | 460 | | | | |
| Val | Asn | Pro | Val | Phe | Thr | Val | Asp | Ala | Lys | Ile | Asp | Gly | Asn | Gly | Phe |
| 465 | | | | | 470 | | | | | 475 | | | | | 480 |
| Thr | Gly | Lys | Ala | Lys | Thr | Ser | Asp | Glu | Gly | Phe | Ala | Leu | Asp | Ser | Gly |
| | | | | 485 | | | | | 490 | | | | | 495 | |
| Ser | Ser | Arg | Tyr | Glu | Asn | Val | Lys | Phe | Asn | Asp | Val | Ala | Val | Ser | Gly |
| | | | 500 | | | | | 505 | | | | | 510 | | |
| Gly | Phe | Tyr | Gly | Pro | Thr | Ala | Ala | Glu | Leu | Gly | Gly | Gln | Phe | His | His |
| | | 515 | | | | | 520 | | | | | 525 | | | |
| Lys | Ser | Glu | Asn | Gly | Ser | Val | Gly | Ala | Val | Phe | Gly | Ala | Lys | Gln | Gln |
| | | 530 | | | | | 535 | | | | | 540 | | | |
| Val | Lys | Lys |
| 545 | | |

( 2 ) INFORMATION FOR SEQ ID NO:3:

( i ) SEQUENCE CHARACTERISTICS:
        ( A ) LENGTH: 1903 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..1777

( x i ) SEQUENCE DESCRIPTION: SEQ ID NO:3:

| | | | | | |
|---|---|---|---|---|---|
| ATGCATTTTA | AACTTAATCC | CTATGCGTTA | GCGTTTACTT | CGCTGTTTCT | TGTCGCTTGT | 60
| TCTGGCGGAA | AAGGAAGTTT | TGATTTAGAA | GATGTCCGGC | CAAATCAAAC | TGCAAAAGCA | 120
| GAAAAAGCAA | CAACCTCTTA | TCAAGATGAG | GAAACGAAGA | AAAAGACAAA | GGAAGAATTA | 180
| GATAAGTTGA | TGGAGCCTGC | TTTGGGGTAT | GAAACTCAAA | TTTTACGGCG | AAATAAGGCT | 240
| CCTAAAACAG | AAACAGGAGA | GAAAAGGAAT | GAGAGAGTTG | TTGAGTTATC | CGAAGATAAA | 300
| ATTACGAAAT | TATACCAAGA | GAGTGTAGAA | ATAATCCCTC | ATTTAGATGA | GCTAAATGGA | 360
| AAAACAACGA | GCAATGATGT | TTATCATTCT | CACGATAGTA | AAAGGCTTGA | TAAGAATAGA | 420
| GATCTCAAAT | ATGTTCGTTC | AGGTTATGTT | TATGATGGGT | CTTTCAATGA | AATACGACGA | 480
| AATGACTCAG | GATTCCATGT | TTTTAAACAG | GGTATAGATG | GCTATGTCTA | TTACCTTGGA | 540
| GTTACTCCAT | CAAAGAGTT | ACCAAAAGGA | AAAGTCATAA | GTTATAAAGG | TACTTGGGAT | 600
| TTTGTAAGTA | ACATCAATTT | AGAGCGTGAA | ATAGATGGAT | TCGACACTTC | AGGTGATGGT | 660
| AAAAATGTAT | CTGCAACATC | TATTACAGAA | ACTGTCAATC | GAGATCATAA | AGTTGGTGAA | 720
| AAACTAGGTG | ATAATGAAGT | TAAAGGGGTA | GCTCATTCTA | GTGAATTTGC | AGTAGATTTT | 780
| GATAACAAAA | AATTGACAGG | TAGTTTATAT | CGTAATGGTT | ATATCAACAG | AAATAAAGCG | 840
| CAAGAAGTAA | CGAAACGCTA | TAGCATTGAA | GCTGATATTG | CAGGCAACCG | TTTTAGGGGA | 900
| AAAGCCAAAG | CAGAAAAAGC | AGGTGATCCG | ATCTTTACTG | ATTCAAATTA | TCTTGAAGGG | 960
| GGATTCTATG | GTCCTAAAGC | TGAAGAAATG | GCAGGGAAGT | TTTTCACAAA | TAATAAATCT | 1020
| CTCTTTGCAG | TATTTGCAGC | TAAAAGTGAA | AACGGCGAGA | CGACCACAGA | ACGAATCATT | 1080
| GATGCAACTA | AAATTGATTT | AACCCAATTT | AATGCTAAAG | AACTCAACAA | TTTTGGTGAT | 1140
| GCCTCTGTTT | TAATTATTGA | TGGACAAAAA | ATAGATCTAG | CAGGTGTCAA | TTTTAAAAAT | 1200
| AGTAAAACGG | TTGAAATCAA | CGGCAAAACA | ATGGTAGCCG | TAGCTTGCTG | TAGTAATCTG | 1260
| GAATATATGA | AATTTGGTCA | ATTGTGGCAA | AAAGAGGGCA | AACAACAAGT | TAAAGATAAT | 1320
| AGTTTATTCC | TACAAGGTGA | ACGTACTGCA | ACGGATAAAA | TGCCCGCAGG | AGGTAACTAT | 1380
| AAGTATGTTG | GAACTTGGGA | TGCACTCGTA | TCTAAAGGGA | CGAACTGGAT | AGCGGAAGCA | 1440
| GATAATAATC | GAGAATCGGG | CTATCGCACT | GAATTTGATG | TTAATTTTAG | TGATAAAAAA | 1500
| GTAAACGGTA | AGTTATTTGA | TAAAGGCGGT | GTAAATCCTG | TATTTACCGT | AGATGCGACA | 1560
| ATTAATGGTA | ATGGCTTTAT | CGGCAGTGCG | AAAACCTCTG | ATAGTGGCTT | TGCTTTAGAT | 1620
| GCAGGCTCTA | GCCAACACGG | AAATGCGGTA | TTTAGTGATA | TAAAAGTCAA | TGGTGGCTTC | 1680
| TATGGTCCAA | CCGCTGGAGA | ACTTGGCGGA | CAATTCCATC | ATAAATCAGA | CAATGGCAGT | 1740
| GTTGGNGCTG | TCTTTGGTGC | AAAAACGACAA | ATAGAAAAAT | AATAAGGAAT | TTGCTATGAA | 1800
| AAATAAATTA | AATCTGATTA | GCCTTGCTCT | TCTTAGCCTA | TTTGCCGTAC | AAAGCTATGC | 1860
| AGAACAAGCG | GTACAATTAA | ATGATGTTTA | TGTCACAGGT | ACC | | 1903

( 2 ) INFORMATION FOR SEQ ID NO:4:

( i ) SEQUENCE CHARACTERISTICS:
        ( A ) LENGTH: 593 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Met His Phe Lys Leu Asn Pro Tyr Ala Leu Ala Phe Thr Ser Leu Phe
1               5                   10                  15

Leu Val Ala Cys Ser Gly Gly Lys Gly Ser Phe Asp Leu Glu Asp Val

|   |   |   | 20 |   |   |   | 25 |   |   |   | 30 |   |   |   |
|---|---|---|---|---|---|---|---|---|---|---|---|---|---|---|
| Arg | Pro | Asn | Gln | Thr | Ala | Lys | Ala | Glu | Lys | Ala | Thr | Thr | Ser | Tyr | Gln |
|   |   | 35 |   |   |   |   | 40 |   |   |   |   | 45 |   |   |   |
| Asp | Glu | Glu | Thr | Lys | Lys | Lys | Thr | Lys | Glu | Glu | Leu | Asp | Lys | Leu | Met |
|   | 50 |   |   |   |   | 55 |   |   |   |   | 60 |   |   |   |   |
| Glu | Pro | Ala | Leu | Gly | Tyr | Glu | Thr | Gln | Ile | Leu | Arg | Arg | Asn | Lys | Ala |
| 65 |   |   |   |   | 70 |   |   |   |   | 75 |   |   |   |   | 80 |
| Pro | Lys | Thr | Glu | Thr | Gly | Glu | Lys | Arg | Asn | Glu | Arg | Val | Val | Glu | Leu |
|   |   |   |   | 85 |   |   |   |   | 90 |   |   |   |   | 95 |   |
| Ser | Glu | Asp | Lys | Ile | Thr | Lys | Leu | Tyr | Gln | Glu | Ser | Val | Glu | Ile | Ile |
|   |   |   | 100 |   |   |   |   | 105 |   |   |   |   | 110 |   |   |
| Pro | His | Leu | Asp | Glu | Leu | Asn | Gly | Lys | Thr | Thr | Ser | Asn | Asp | Val | Tyr |
|   |   | 115 |   |   |   |   | 120 |   |   |   |   | 125 |   |   |   |
| His | Ser | His | Asp | Ser | Lys | Arg | Leu | Asp | Lys | Asn | Arg | Asp | Leu | Lys | Tyr |
|   | 130 |   |   |   |   | 135 |   |   |   |   | 140 |   |   |   |   |
| Val | Arg | Ser | Gly | Tyr | Val | Tyr | Asp | Gly | Ser | Phe | Asn | Glu | Ile | Arg | Arg |
| 145 |   |   |   |   | 150 |   |   |   |   | 155 |   |   |   |   | 160 |
| Asn | Asp | Ser | Gly | Phe | His | Val | Phe | Lys | Gln | Gly | Ile | Asp | Gly | Tyr | Val |
|   |   |   |   | 165 |   |   |   |   | 170 |   |   |   |   | 175 |   |
| Tyr | Tyr | Leu | Gly | Val | Thr | Pro | Ser | Lys | Glu | Leu | Pro | Lys | Gly | Lys | Val |
|   |   |   | 180 |   |   |   |   | 185 |   |   |   |   | 190 |   |   |
| Ile | Ser | Tyr | Lys | Gly | Thr | Trp | Asp | Phe | Val | Ser | Asn | Ile | Asn | Leu | Glu |
|   |   |   | 195 |   |   |   |   | 200 |   |   |   |   | 205 |   |   |
| Arg | Glu | Ile | Asp | Gly | Phe | Asp | Thr | Ser | Gly | Asp | Gly | Lys | Asn | Val | Ser |
|   | 210 |   |   |   |   | 215 |   |   |   |   | 220 |   |   |   |   |
| Ala | Thr | Ser | Ile | Thr | Glu | Thr | Val | Asn | Arg | Asp | His | Lys | Val | Gly | Glu |
| 225 |   |   |   |   | 230 |   |   |   |   | 235 |   |   |   |   | 240 |
| Lys | Leu | Gly | Asp | Asn | Glu | Val | Lys | Gly | Val | Ala | His | Ser | Ser | Glu | Phe |
|   |   |   |   | 245 |   |   |   |   | 250 |   |   |   |   | 255 |   |
| Ala | Val | Asp | Phe | Asp | Asn | Lys | Lys | Leu | Thr | Gly | Ser | Leu | Tyr | Arg | Asn |
|   |   |   | 260 |   |   |   |   | 265 |   |   |   |   | 270 |   |   |
| Gly | Tyr | Ile | Asn | Arg | Asn | Lys | Ala | Gln | Glu | Val | Thr | Lys | Arg | Tyr | Ser |
|   |   | 275 |   |   |   |   | 280 |   |   |   |   | 285 |   |   |   |
| Ile | Glu | Ala | Asp | Ile | Ala | Gly | Asn | Arg | Phe | Arg | Gly | Lys | Ala | Lys | Ala |
|   | 290 |   |   |   |   | 295 |   |   |   |   | 300 |   |   |   |   |
| Glu | Lys | Ala | Gly | Asp | Pro | Ile | Phe | Thr | Asp | Ser | Asn | Tyr | Leu | Glu | Gly |
| 305 |   |   |   |   | 310 |   |   |   |   | 315 |   |   |   |   | 320 |
| Gly | Phe | Tyr | Gly | Pro | Lys | Ala | Glu | Glu | Met | Ala | Gly | Lys | Phe | Phe | Thr |
|   |   |   |   | 325 |   |   |   |   | 330 |   |   |   |   | 335 |   |
| Asn | Asn | Lys | Ser | Leu | Phe | Ala | Val | Phe | Ala | Ala | Lys | Ser | Glu | Asn | Gly |
|   |   |   | 340 |   |   |   |   | 345 |   |   |   |   | 350 |   |   |
| Glu | Thr | Thr | Thr | Glu | Arg | Ile | Ile | Asp | Ala | Thr | Lys | Ile | Asp | Leu | Thr |
|   |   | 355 |   |   |   |   | 360 |   |   |   |   | 365 |   |   |   |
| Gln | Phe | Asn | Ala | Lys | Glu | Leu | Asn | Asn | Phe | Gly | Asp | Ala | Ser | Val | Leu |
|   | 370 |   |   |   |   | 375 |   |   |   |   | 380 |   |   |   |   |
| Ile | Ile | Asp | Gly | Gln | Lys | Ile | Asp | Leu | Ala | Gly | Val | Asn | Phe | Lys | Asn |
| 385 |   |   |   |   | 390 |   |   |   |   | 395 |   |   |   |   | 400 |
| Ser | Lys | Thr | Val | Glu | Ile | Asn | Gly | Lys | Thr | Met | Val | Ala | Val | Ala | Cys |
|   |   |   |   | 405 |   |   |   |   | 410 |   |   |   |   | 415 |   |
| Cys | Ser | Asn | Leu | Glu | Tyr | Met | Lys | Phe | Gly | Gln | Leu | Trp | Gln | Lys | Glu |
|   |   |   | 420 |   |   |   |   | 425 |   |   |   |   | 430 |   |   |
| Gly | Lys | Gln | Gln | Val | Lys | Asp | Asn | Ser | Leu | Phe | Leu | Gln | Gly | Glu | Arg |
|   |   | 435 |   |   |   |   | 440 |   |   |   |   | 445 |   |   |   |

| Thr | Ala | Thr | Asp | Lys | Met | Pro | Ala | Gly | Gly | Asn | Tyr | Lys | Tyr | Val | Gly |
|---|---|---|---|---|---|---|---|---|---|---|---|---|---|---|---|
| | 450 | | | | 455 | | | | | 460 | | | | | |

| Thr | Trp | Asp | Ala | Leu | Val | Ser | Lys | Gly | Thr | Asn | Trp | Ile | Ala | Glu | Ala |
|---|---|---|---|---|---|---|---|---|---|---|---|---|---|---|---|
| 465 | | | | | 470 | | | | 475 | | | | | | 480 |

| Asp | Asn | Asn | Arg | Glu | Ser | Gly | Tyr | Arg | Thr | Glu | Phe | Asp | Val | Asn | Phe |
|---|---|---|---|---|---|---|---|---|---|---|---|---|---|---|---|
| | | | | 485 | | | | | 490 | | | | | 495 | |

| Ser | Asp | Lys | Lys | Val | Asn | Gly | Lys | Leu | Phe | Asp | Lys | Gly | Gly | Val | Asn |
|---|---|---|---|---|---|---|---|---|---|---|---|---|---|---|---|
| | | | 500 | | | | | 505 | | | | | 510 | | |

| Pro | Val | Phe | Thr | Val | Asp | Ala | Thr | Ile | Asn | Gly | Asn | Gly | Phe | Ile | Gly |
|---|---|---|---|---|---|---|---|---|---|---|---|---|---|---|---|
| | | 515 | | | | | 520 | | | | | 525 | | | |

| Ser | Ala | Lys | Thr | Ser | Asp | Ser | Gly | Phe | Ala | Leu | Asp | Ala | Gly | Ser | Ser |
|---|---|---|---|---|---|---|---|---|---|---|---|---|---|---|---|
| | 530 | | | | | 535 | | | | | 540 | | | | |

| Gln | His | Gly | Asn | Ala | Val | Phe | Ser | Asp | Ile | Lys | Val | Asn | Gly | Gly | Phe |
|---|---|---|---|---|---|---|---|---|---|---|---|---|---|---|---|
| 545 | | | | | 550 | | | | | 555 | | | | | 560 |

| Tyr | Gly | Pro | Thr | Ala | Gly | Glu | Leu | Gly | Gly | Gln | Phe | His | His | Lys | Ser |
|---|---|---|---|---|---|---|---|---|---|---|---|---|---|---|---|
| | | | | 565 | | | | | 570 | | | | | 575 | |

| Asp | Asn | Gly | Ser | Val | Gly | Ala | Val | Phe | Gly | Ala | Lys | Arg | Gln | Ile | Glu |
|---|---|---|---|---|---|---|---|---|---|---|---|---|---|---|---|
| | | | 580 | | | | | 585 | | | | | 590 | | |

| Lys |
|---|

( 2 ) INFORMATION FOR SEQ ID NO:5:

( i ) SEQUENCE CHARACTERISTICS:
        ( A ) LENGTH: 593 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

| Met | His | Phe | Lys | Leu | Asn | Pro | Tyr | Ala | Leu | Ala | Phe | Thr | Ser | Leu | Phe |
|---|---|---|---|---|---|---|---|---|---|---|---|---|---|---|---|
| 1 | | | | 5 | | | | | 10 | | | | | 15 | |

| Leu | Val | Ala | Cys | Ser | Gly | Gly | Lys | Gly | Ser | Phe | Asp | Leu | Glu | Asp | Val |
|---|---|---|---|---|---|---|---|---|---|---|---|---|---|---|---|
| | | | 20 | | | | | 25 | | | | | 30 | | |

| Arg | Pro | Asn | Gln | Thr | Ala | Lys | Ala | Glu | Lys | Ala | Thr | Thr | Ser | Tyr | Gln |
|---|---|---|---|---|---|---|---|---|---|---|---|---|---|---|---|
| | | | 35 | | | | | 40 | | | | | 45 | | |

| Asp | Glu | Glu | Thr | Lys | Lys | Lys | Thr | Lys | Glu | Glu | Leu | Asp | Lys | Leu | Met |
|---|---|---|---|---|---|---|---|---|---|---|---|---|---|---|---|
| | 50 | | | | | 55 | | | | | 60 | | | | |

| Glu | Pro | Ala | Leu | Gly | Tyr | Glu | Thr | Gln | Ile | Leu | Arg | Arg | Asn | Lys | Ala |
|---|---|---|---|---|---|---|---|---|---|---|---|---|---|---|---|
| 65 | | | | | 70 | | | | | 75 | | | | | 80 |

| Pro | Lys | Thr | Glu | Thr | Gly | Glu | Lys | Arg | Asn | Glu | Arg | Val | Val | Glu | Leu |
|---|---|---|---|---|---|---|---|---|---|---|---|---|---|---|---|
| | | | | 85 | | | | | 90 | | | | | 95 | |

| Ser | Glu | Asp | Lys | Ile | Thr | Lys | Leu | Tyr | Gln | Glu | Ser | Val | Glu | Ile | Ile |
|---|---|---|---|---|---|---|---|---|---|---|---|---|---|---|---|
| | | | 100 | | | | | 105 | | | | | 110 | | |

| Pro | His | Leu | Asp | Glu | Leu | Asn | Gly | Lys | Thr | Thr | Ser | Asn | Asp | Val | Tyr |
|---|---|---|---|---|---|---|---|---|---|---|---|---|---|---|---|
| | | 115 | | | | | 120 | | | | | 125 | | | |

| His | Ser | His | Asp | Ser | Lys | Arg | Leu | Asp | Lys | Asn | Arg | Asp | Leu | Lys | Tyr |
|---|---|---|---|---|---|---|---|---|---|---|---|---|---|---|---|
| | 130 | | | | | 135 | | | | | 140 | | | | |

| Val | Arg | Ser | Gly | Tyr | Val | Tyr | Asp | Gly | Ser | Phe | Asn | Glu | Ile | Arg | Arg |
|---|---|---|---|---|---|---|---|---|---|---|---|---|---|---|---|
| 145 | | | | | 150 | | | | | 155 | | | | | 160 |

| Asn | Asp | Ser | Gly | Phe | His | Val | Phe | Lys | Gln | Gly | Ile | Asp | Gly | Tyr | Val |
|---|---|---|---|---|---|---|---|---|---|---|---|---|---|---|---|
| | | | | 165 | | | | | 170 | | | | | 175 | |

| Tyr | Tyr | Leu | Gly | Val | Thr | Pro | Ser | Lys | Glu | Leu | Pro | Lys | Gly | Lys | Val |
|---|---|---|---|---|---|---|---|---|---|---|---|---|---|---|---|
| | | | 180 | | | | | 185 | | | | | 190 | | |

| Ile | Ser | Tyr | Lys | Gly | Thr | Trp | Asp | Phe | Val | Ser | Asn | Ile | Asn | Leu | Glu |
|---|---|---|---|---|---|---|---|---|---|---|---|---|---|---|---|
| | | 195 | | | | | 200 | | | | | 205 | | | |

| Arg | Glu | Ile | Asp | Gly | Phe | Asp | Thr | Ser | Gly | Asp | Gly | Lys | Asn | Val | Ser |
|---|---|---|---|---|---|---|---|---|---|---|---|---|---|---|---|

-continued

```
              210                          215                          220
Ala  Thr  Ser  Ile  Thr  Glu  Thr  Val  Asn  Arg  Asp  His  Lys  Val  Gly  Glu
225                      230                      235                      240

Lys  Leu  Gly  Asp  Asn  Glu  Val  Lys  Gly  Val  Ala  His  Ser  Ser  Glu  Phe
                    245                      250                      255

Ala  Val  Asp  Phe  Asp  Asn  Lys  Lys  Leu  Thr  Gly  Ser  Leu  Tyr  Arg  Asn
               260                      265                      270

Gly  Tyr  Ile  Asn  Arg  Asn  Lys  Ala  Gln  Glu  Val  Thr  Lys  Arg  Tyr  Ser
          275                      280                      285

Ile  Glu  Ala  Asp  Ile  Ala  Gly  Asn  Arg  Phe  Arg  Gly  Lys  Ala  Lys  Ala
     290                      295                      300

Glu  Lys  Ala  Gly  Asp  Pro  Ile  Phe  Thr  Asp  Ser  Asn  Tyr  Leu  Glu  Gly
305                      310                      315                      320

Gly  Phe  Tyr  Gly  Pro  Lys  Ala  Glu  Glu  Met  Ala  Gly  Lys  Phe  Phe  Thr
                    325                      330                      335

Asn  Asn  Lys  Ser  Leu  Phe  Ala  Val  Phe  Ala  Ala  Lys  Ser  Glu  Asn  Gly
               340                      345                      350

Glu  Thr  Thr  Thr  Glu  Arg  Ile  Ile  Asp  Ala  Thr  Lys  Ile  Asp  Leu  Thr
          355                      360                      365

Gln  Phe  Asn  Ala  Lys  Glu  Leu  Asn  Asn  Phe  Gly  Asp  Ala  Ser  Val  Leu
     370                      375                      380

Ile  Ile  Asp  Gly  Gln  Lys  Ile  Asp  Leu  Ala  Gly  Val  Asn  Phe  Lys  Asn
385                      390                      395                      400

Ser  Lys  Thr  Val  Glu  Ile  Asn  Gly  Lys  Thr  Met  Val  Ala  Val  Ala  Cys
                    405                      410                      415

Cys  Ser  Asn  Leu  Glu  Tyr  Met  Lys  Phe  Gly  Gln  Leu  Trp  Gln  Lys  Glu
               420                      425                      430

Gly  Lys  Gln  Gln  Val  Lys  Asp  Asn  Ser  Leu  Phe  Leu  Gln  Gly  Glu  Arg
          435                      440                      445

Thr  Ala  Thr  Asp  Lys  Met  Pro  Ala  Gly  Gly  Asn  Tyr  Lys  Tyr  Val  Gly
     450                      455                      460

Thr  Trp  Asp  Ala  Leu  Val  Ser  Lys  Gly  Thr  Asn  Trp  Ile  Ala  Glu  Ala
465                      470                      475                      480

Asp  Asn  Asn  Arg  Glu  Ser  Gly  Tyr  Arg  Thr  Glu  Phe  Asp  Val  Asn  Phe
                    485                      490                      495

Ser  Asp  Lys  Lys  Val  Asn  Gly  Lys  Leu  Phe  Asp  Lys  Gly  Gly  Val  Asn
               500                      505                      510

Pro  Val  Phe  Thr  Val  Asp  Ala  Thr  Ile  Asn  Gly  Asn  Gly  Phe  Ile  Gly
          515                      520                      525

Ser  Ala  Lys  Thr  Ser  Asp  Ser  Gly  Phe  Ala  Leu  Asp  Ala  Gly  Ser  Ser
     530                      535                      540

Gln  His  Gly  Asn  Ala  Val  Phe  Ser  Asp  Ile  Lys  Val  Asn  Gly  Gly  Phe
545                      550                      555                      560

Tyr  Gly  Pro  Thr  Ala  Gly  Glu  Leu  Gly  Gly  Gln  Phe  His  His  Lys  Ser
                    565                      570                      575

Asp  Asn  Gly  Ser  Val  Gly  Ala  Val  Phe  Gly  Ala  Lys  Arg  Gln  Ile  Glu
               580                      585                      590

Lys
```

( 2 ) INFORMATION FOR SEQ ID NO:6:

( i ) SEQUENCE CHARACTERISTICS:
( A ) LENGTH: 547 amino acids
( B ) TYPE: amino acid
( C ) STRANDEDNESS: single ( D ) TOPOLOGY: linear ( x i ) SEQUENCE DESCRIPTION: SEQ ID NO:6:

| Met | His | Phe | Lys | Leu | Asn | Pro | Tyr | Ala | Leu | Ala | Phe | Thr | Ser | Leu | Phe |
|---|---|---|---|---|---|---|---|---|---|---|---|---|---|---|---|
| 1 | | | | 5 | | | | | 10 | | | | | 15 | |
| Leu | Val | Ala | Cys | Ser | Gly | Gly | Lys | Gly | Ser | Phe | Asp | Leu | Glu | Asp | Val |
| | | | 20 | | | | 25 | | | | | 30 | | | |
| Arg | Pro | Asn | Lys | Thr | Thr | Gly | Val | Ser | Lys | Glu | Glu | Tyr | Lys | Asp | Val |
| | | | 35 | | | | 40 | | | | | 45 | | | |
| Glu | Thr | Ala | Lys | Lys | Glu | Lys | Glu | Gln | Leu | Gly | Glu | Leu | Met | Glu | Pro |
| | | | 50 | | | | 55 | | | | | 60 | | | |
| Ala | Leu | Gly | Tyr | Val | Val | Lys | Val | Pro | Val | Ser | Ser | Phe | Glu | Asn | Lys |
| 65 | | | | 70 | | | | | 75 | | | | | 80 | |
| Lys | Val | Asp | Ile | Ser | Asp | Ile | Glu | Val | Ile | Thr | Asn | Gly | Asn | Leu | Asp |
| | | | | 85 | | | | | 90 | | | | | 95 | |
| Asp | Val | Pro | Tyr | Lys | Ala | Asn | Ser | Ser | Lys | Tyr | Asn | Tyr | Pro | Asp | Ile |
| | | | 100 | | | | | 105 | | | | | 110 | | |
| Lys | Thr | Lys | Asp | Ser | Ser | Leu | Gln | Tyr | Val | Arg | Ser | Gly | Tyr | Val | Ile |
| | | 115 | | | | | 120 | | | | | 125 | | | |
| Asp | Gly | Glu | His | Ser | Gly | Ser | Asn | Glu | Lys | Gly | Tyr | Val | Tyr | Tyr | Lys |
| | 130 | | | | 135 | | | | | 140 | | | | | |
| Gly | Asn | Ser | Pro | Ala | Lys | Glu | Leu | Pro | Val | Asn | Gln | Leu | Leu | Thr | Tyr |
| 145 | | | | | 150 | | | | | 155 | | | | | 160 |
| Thr | Gly | Ser | Trp | Asp | Phe | Thr | Ser | Asn | Ala | Asn | Leu | Asn | Asn | Glu | Glu |
| | | | | 165 | | | | | 170 | | | | | 175 | |
| Gly | Arg | Pro | Asn | Tyr | Leu | Asn | Asp | Asp | Tyr | Tyr | Thr | Lys | Phe | Ile | Gly |
| | | | 180 | | | | | 185 | | | | | 190 | | |
| Lys | Arg | Val | Gly | Leu | Val | Ser | Gly | Asp | Ala | Lys | Pro | Ala | Lys | His | Lys |
| | | 195 | | | | | 200 | | | | | 205 | | | |
| Tyr | Thr | Ser | Gln | Phe | Glu | Val | Asp | Phe | Ala | Thr | Lys | Lys | Met | Thr | Gly |
| | | 210 | | | | | 215 | | | | | 220 | | | |
| Lys | Leu | Ser | Asp | Lys | Glu | Lys | Thr | Ile | Tyr | Thr | Val | Asn | Ala | Asp | Ile |
| 225 | | | | | 230 | | | | | 235 | | | | | 240 |
| Arg | Gly | Asn | Arg | Phe | Thr | Gly | Ala | Ala | Thr | Ala | Ser | Asp | Lys | Asn | Lys |
| | | | | 245 | | | | | 250 | | | | | 255 | |
| Gly | Lys | Gly | Glu | Ser | Tyr | Asn | Phe | Phe | Ser | Ala | Asp | Ser | Gln | Ser | Leu |
| | | | 260 | | | | | 265 | | | | | 270 | | |
| Glu | Gly | Gly | Phe | Tyr | Gly | Pro | Lys | Ala | Glu | Glu | Met | Ala | Gly | Lys | Phe |
| | | 275 | | | | | 280 | | | | | 285 | | | |
| Val | Ala | Asn | Asp | Lys | Ser | Leu | Phe | Ala | Val | Phe | Ser | Ala | Lys | His | Asn |
| | 290 | | | | | 295 | | | | | 300 | | | | |
| Gly | Ser | Asn | Val | Asn | Thr | Val | Arg | Ile | Ile | Asp | Ala | Ser | Lys | Ile | Asp |
| 305 | | | | | 310 | | | | | 315 | | | | | 320 |
| Leu | Thr | Asn | Phe | Ser | Ile | Ser | Glu | Leu | Asn | Asn | Phe | Gly | Asp | Ala | Ser |
| | | | | 325 | | | | | 330 | | | | | 335 | |
| Val | Leu | Ile | Ile | Asp | Gly | Lys | Lys | Ile | Lys | Leu | Ala | Gly | Ser | Gly | Phe |
| | | | 340 | | | | | 345 | | | | | 350 | | |
| Thr | Asn | Lys | His | Thr | Ile | Glu | Ile | Asn | Gly | Lys | Thr | Met | Val | Ala | Val |
| | | 355 | | | | | 360 | | | | | 365 | | | |
| Ala | Cys | Cys | Ser | Asn | Leu | Glu | Tyr | Met | Lys | Phe | Gly | Gln | Leu | Trp | Gln |
| | 370 | | | | | 375 | | | | | 380 | | | | |
| Gln | Ala | Glu | Gly | Gly | Lys | Pro | Glu | Asn | Asn | Ser | Leu | Phe | Leu | Gln | Gly |
| 385 | | | | | 390 | | | | | 395 | | | | | 400 |
| Glu | Arg | Thr | Ala | Thr | Asp | Lys | Met | Pro | Lys | Gly | Gly | Asn | Tyr | Lys | Tyr |

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 405 |     |     |     | 410 |     |     |     | 415 |     |     |
| Ile | Gly | Thr | Trp | Asp | Ala | Gln | Val | Ser | Lys | Glu | Asn | Asn | Trp | Val | Ala |
|     |     |     | 420 |     |     |     |     | 425 |     |     |     |     | 430 |     |     |
| Thr | Ala | Asp | Asp | Asp | Arg | Lys | Ala | Gly | Tyr | Arg | Thr | Glu | Phe | Asp | Val |
|     |     | 435 |     |     |     |     | 440 |     |     |     |     | 445 |     |     |     |
| Asp | Phe | Gly | Asn | Lys | Asn | Leu | Ser | Gly | Lys | Leu | Phe | Asp | Lys | Asn | Gly |
|     |     | 450 |     |     |     |     | 455 |     |     |     |     | 460 |     |     |     |
| Val | Asn | Pro | Val | Phe | Thr | Val | Asp | Ala | Lys | Ile | Asp | Gly | Asn | Gly | Phe |
| 465 |     |     |     |     | 470 |     |     |     |     | 475 |     |     |     |     | 480 |
| Thr | Gly | Lys | Ala | Lys | Thr | Ser | Asp | Glu | Gly | Phe | Ala | Leu | Asp | Ser | Gly |
|     |     |     |     | 485 |     |     |     |     | 490 |     |     |     |     | 495 |     |
| Ser | Ser | Arg | Tyr | Glu | Asn | Val | Lys | Phe | Asn | Asp | Val | Ala | Val | Ser | Gly |
|     |     |     | 500 |     |     |     |     | 505 |     |     |     |     | 510 |     |     |
| Gly | Phe | Tyr | Gly | Pro | Thr | Ala | Ala | Glu | Leu | Gly | Gly | Gln | Phe | His | His |
|     |     |     | 515 |     |     |     |     | 520 |     |     |     |     | 525 |     |     |
| Lys | Ser | Glu | Asn | Gly | Ser | Val | Gly | Ala | Val | Phe | Gly | Ala | Lys | Gln | Gln |
|     |     |     | 530 |     |     |     | 535 |     |     |     |     | 540 |     |     |     |
| Val | Lys | Lys |     |     |     |     |     |     |     |     |     |     |     |     |     |
| 545 |     |     |     |     |     |     |     |     |     |     |     |     |     |     |     |

( 2 ) INFORMATION FOR SEQ ID NO:7:

( i ) SEQUENCE CHARACTERISTICS:
        ( A ) LENGTH: 265 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| CTGTTATAGA | TCTAGGAAAA | GCAAGTTTAG | GTTTGGACAT | TATCTCTGGT | TTACTTTCTG | 60 |
| GAGCATCTGC | AGGTCTCATT | TTAGCAGATA | AAGAGGCTTC | AACAGAAAAG | AAAGCTGCCG | 120 |
| CAGGTGTAGA | ATTTGCTAAC | CAAATTATAG | GTAATGTAAC | AAAAGCGGTC | TCATCTTACA | 180 |
| TTCTTGCCCA | ACGAGTCGCT | TCAGGTTTGT | CTTCAACTGG | TCCTGTCGCT | GCATTAATCG | 240 |
| CATCTACAGT | TGCACTAGCT | GTTAG | | | | 265 |

( 2 ) INFORMATION FOR SEQ ID NO:8:

( i ) SEQUENCE CHARACTERISTICS:
        ( A ) LENGTH: 1649 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | |
|---|---|---|---|---|---|
| GGATCCTGTT | CTTGGTGAAA | GTGTGGAACT | TAAAGTTAAC | TTATGTTTAG | AGAAAAAGG | 60 |
| ATGGTATCTA | GAGCAAGGTC | CAGTGTGTGA | AGAAAATAC | GTATGAATG | AACCGGAATG | 120 |
| TATTAAATGG | CGAGCAAAAT | ATAGTAAGCC | AAATGTGCAA | CCTTGGGGAT | AATAGTCATT | 180 |
| TAAGTGTTTT | AAAAATTTAA | TTTCAGAAAT | TGTAATGGA | TACAATGAAT | ACAGAAAATA | 240 |
| ATTAATGTTT | AAAATCAAGC | ACTAAATGAT | TTTGTAATGG | CACTTTAGCT | GGGGTTATAT | 300 |
| GAAGTAAATT | CTTAATGTGT | AGAAAATCAA | ACCTAATCTG | ACAGTCCCG | TTTAAAATTA | 360 |
| CCGTGTCTGT | CAGATTAATT | TGAGCTTAAA | TTCTTTTCTG | CCCAAATCCG | TTTTCCATCA | 420 |
| AGTAATGTTG | CCATCGGTGT | TCTGCCACAG | CACACTTTTC | CTTGATGTGT | TCGATGGTGA | 480 |
| TTATAATACA | TTAACCACTC | ATCTAAATCA | GCTTGTAATG | TCGCTAAATC | CGTATATATT | 540 |
| TTCTTCCTAA | ATGCGACTTG | GTAAAATTCT | TGTAAGATAG | TCTTATGAAA | ACGTTCACAG | 600 |

-continued

| | | | | | |
|---|---|---|---|---|---|
| ATACCATTCG | TCTGTGGATG | CTTCACTTTC | GTTTTAGTAT | GCTCTATGTC | ATTTATCGCT | 660
| AAATAAAGCT | CATAATCGTG | ATTTTCCACT | TTGCCACAAT | ATTCACTGCC | ACGGTCGGTG | 720
| AGAATACGCA | ACATCGGTAA | TCCTTGGGCT | TCAAAGAACG | GCAGTACTTT | ATCATTGAGC | 780
| ATATCTGCAG | CGGCAATTGC | GGTTTTCATT | GTGTAGAGCT | TTGCAAAAGC | AACCTTACTA | 840
| TAAGTATCAA | CAAATGTTTG | CTGATAAATG | CGTCCAACAC | CTTTTAAATT | ACCTACATAA | 900
| AAGGTATCTT | GTGAACCTAA | ATAGCCCGGA | TGAGCGGTTT | CAATTCTCC | ACTCGATATA | 960
| TCATCCTCTT | TCTTACGTTC | TAGGGCTTGG | ACTTGACTTT | CATTTAGAAT | AATGCCTTTC | 1020
| TCAGCCACTT | CTTTCTCTAG | TGCATTTAAA | CGCTGTTTAA | AGTTAGTAAG | ATTATGACGT | 1080
| AGCCAAATGG | AACGAACACC | ACCGGCTGAA | ACAAACACAC | CTTGCTTGCG | AAGTTCGTTA | 1140
| CTCACTCGAA | CTTGTCCGTA | AGCTGGAAAA | TCTAGAGCAA | ATTTACAAC | AGCTTGCTCA | 1200
| ATGTGCTCGT | CTACTCGATT | TTTGATATTC | GGTACCCGAC | GAGTTTGCTT | AACTAATGCT | 1260
| TCAACACCGC | CTTGCGCTAC | GGCTTGTTGA | TAGCGATAGA | ATGTATCTCG | GCTCATTCCC | 1320
| ATCGCTTTAC | AAGCTTGAGA | AATGTTTCCG | AGTTCTTCTG | CTAAATTGAG | TAAACCGGTC | 1380
| TTGTGTTTAA | TGAGCGGATT | GTTAGAATAA | AACATGAGAG | TTTCCTTTTT | TGTTTAGATT | 1440
| GAATTTAGA | CACTCATATT | CTAAACGGGA | AACTCTCATT | TTTATAATGA | TTTGTCAGAT | 1500
| CAAGTCTGAT | CTTCTACAAA | TATTATCCCC | ATTTATGGAG | TTCGTCTTTT | AGATGAACTC | 1560
| CTATTGTTTA | TAATTCGATA | AAATTAGCTT | TCTCACAGCA | ACTCAGCAAT | GGGTTGCTTT | 1620
| TTTATTTGAC | AGAAAAACAA | CGTAGATCT | | | | 1649

( 2 ) INFORMATION FOR SEQ ID NO:9:

( i ) SEQUENCE CHARACTERISTICS:
        ( A ) LENGTH: 252 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | | | | | |
|---|---|---|---|---|---|
| CTTAATGATA | TAACAGCGGT | CAAATTCTAA | AATCTTTTGC | AATGTGCAAC | TTTTATTAGG | 60
| ATTTCTAGAT | GGAAAAGGTT | TGTCTTTAAC | ATCATGGTTA | ATCGCAGCAA | AATCATTAGA | 120
| TTTAAAAGCA | AAGGCTATTA | ATAAAGCCGT | TGAGCGTTTA | CCTTTTGTTA | ATTTACCTGC | 180
| ACTTATCTGG | AGGGAAGATG | GAAAACATTT | TATCTTAGTA | AAGATAGATA | AAGATAAAAA | 240
| ACGCTATTTA | AC | | | | | 252

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGTAGAAAAT    CAAACCTAAT    CTGACA                                                                 26

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ACATCTTCTA GTCTGAACTA GACTGT 26